(12) United States Patent
Kinsho et al.

(10) Patent No.: US 8,795,955 B2
(45) Date of Patent: Aug. 5, 2014

(54) NAPHTHALENE DERIVATIVE, RESIST BOTTOM LAYER MATERIAL, RESIST BOTTOM LAYER FORMING METHOD, AND PATTERNING PROCESS

(75) Inventors: Takeshi Kinsho, Joetsu (JP); Katsuya Takemura, Joetsu (JP); Daisuke Kori, Joetsu (JP); Takeru Watanabe, Joetsu (JP); Tsutomu Ogihara, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 272 days.

(21) Appl. No.: 13/165,536

(22) Filed: Jun. 21, 2011

(65) Prior Publication Data

US 2011/0311920 A1 Dec. 22, 2011

(30) Foreign Application Priority Data

Jun. 21, 2010 (JP) ................................. 2010-140533

(51) Int. Cl.
*G03F 7/20* (2006.01)
*C07D 311/78* (2006.01)
*B05D 3/12* (2006.01)
*C08G 65/00* (2006.01)
*B05D 3/10* (2006.01)
*C07C 43/20* (2006.01)
*C07D 307/77* (2006.01)
*C07C 43/275* (2006.01)
*C09D 201/06* (2006.01)

(52) U.S. Cl.
CPC ............ *C07C 43/275* (2013.01); *C07D 311/78* (2013.01); *B05D 3/12* (2013.01); *C08G 65/00* (2013.01); *B05D 3/10* (2013.01); *C07C 43/20* (2013.01); *C07D 307/77* (2013.01); *C07C 2103/18* (2013.01); *C09D 201/06* (2013.01)
USPC ........... 430/323; 568/633; 549/382; 549/456; 528/86; 427/385.5; 427/240

(58) Field of Classification Search
CPC .. C07D 311/82; C07D 307/92; C07D 307/77; C07C 43/275; C07C 493/00; C08G 65/40
USPC .............. 568/633; 549/224, 456, 382; 528/86
See application file for complete search history.

(56) References Cited

U.S. PATENT DOCUMENTS

| | | | |
|---|---|---|---|
| 5,972,560 A | 10/1999 | Kaneko et al. | |
| 6,042,989 A | 3/2000 | Schaedeli et al. | |
| 6,420,088 B1 | 7/2002 | Angelopoulos et al. | |
| 6,506,497 B1 | 1/2003 | Kennedy et al. | |
| 6,576,562 B2 | 6/2003 | Ohuchi et al. | |
| 6,623,909 B2 | 9/2003 | Hatakeyama et al. | |
| 6,730,453 B2 | 5/2004 | Nakashima et al. | |
| 6,749,765 B2 | 6/2004 | Rutter, Jr. et al. | |
| 6,852,791 B2 | 2/2005 | Kawaguchi et al. | |
| 7,094,708 B2 | 8/2006 | Kato et al. | |
| 7,156,923 B2 | 1/2007 | Kato et al. | |
| 7,163,778 B2 | 1/2007 | Hatakeyama et al. | |
| 7,202,013 B2 | 4/2007 | Ogihara et al. | |
| 7,214,743 B2 | 5/2007 | Hatakeyama et al. | |
| 7,303,785 B2 | 12/2007 | Ogihara et al. | |
| 7,303,855 B2 | 12/2007 | Hatakeyama et al. | |
| 7,358,025 B2 | 4/2008 | Hatakeyama | |
| 7,416,833 B2 | 8/2008 | Hatakeyama et al. | |
| 7,476,485 B2 | 1/2009 | Hatakeyama et al. | |
| 7,510,820 B2 | 3/2009 | Hatakeyama et al. | |
| 7,537,880 B2 | 5/2009 | Harada et al. | |
| 7,541,134 B2 | 6/2009 | Iwabuchi et al. | |
| 7,585,613 B2 | 9/2009 | Ogihara et al. | |
| 7,632,624 B2 | 12/2009 | Hatakeyama et al. | |
| 2007/0134916 A1 | 6/2007 | Iwabuchi et al. | |

FOREIGN PATENT DOCUMENTS

| | | |
|---|---|---|
| JP | 3-504247 A | 9/1991 |
| JP | 6-118651 A | 4/1994 |
| JP | 9-110938 A | 4/1997 |
| JP | 10-324748 A | 12/1998 |

(Continued)

OTHER PUBLICATIONS

W. Brunsvold et al., "Evaluation of a Deep UV Bilayer Resist for Sub-Half Micron Lithography", SPIE vol. 1925, 1993, pp. 377-387.

(Continued)

*Primary Examiner* — Rosalynd Keys

(74) *Attorney, Agent, or Firm* — Westerman, Hattori, Daniels & Adrian, LLP

(57) ABSTRACT

A naphthalene derivative having formula (1) is provided wherein cyclic structures Ar1 and Ar2 denote a benzene or naphthalene ring, X is a single bond or $C_1$-$C_{20}$ alkylene, m is 0 or 1, and n is such a natural number as to provide a molecular weight of up to 100,000. A material comprising the naphthalene derivative or a polymer comprising the naphthalene derivative is spin coated to form a resist bottom layer having improved properties. A pattern forming process in which a resist bottom layer formed by spin coating is combined with an inorganic hard mask formed by CVD is available.

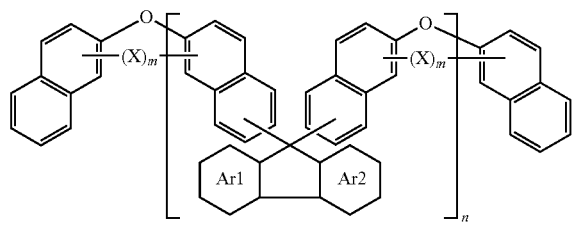

(1)

14 Claims, 6 Drawing Sheets

(56) References Cited

FOREIGN PATENT DOCUMENTS

| | | | |
|---|---|---|---|
| JP | 11-154638 A | 6/1999 | |
| JP | 11-302382 A | 11/1999 | |
| JP | 2001-040293 A | 2/2001 | |
| JP | 2002-014474 A | 1/2002 | |
| JP | 2002-047430 A | 2/2002 | |
| JP | 2002-055456 A | 2/2002 | |
| JP | 2002-214777 A | 7/2002 | |
| JP | 2002-334869 A | 11/2002 | |
| JP | 2004-205658 A | 7/2004 | |
| JP | 2004-205676 A | 7/2004 | |
| JP | 2004-205685 A | 7/2004 | |
| JP | 2004-310019 A | 11/2004 | |
| JP | 2004-354554 A | 12/2004 | |
| JP | 2005-010431 A | 1/2005 | |
| JP | 2005-015779 A | 1/2005 | |
| JP | 2005-018054 A | 1/2005 | |
| JP | 2005-128509 A | 5/2005 | |
| JP | 2005-250434 A | 9/2005 | |
| JP | 2005-352104 A | 12/2005 | |
| JP | 2006-053543 A | 2/2006 | |
| JP | 2006-227391 A | 8/2006 | |
| JP | 2006-259249 A | 9/2006 | |
| JP | 2006-259482 A | 9/2006 | |
| JP | 2006-285095 A | 10/2006 | |
| JP | 2006-293298 A | 10/2006 | |
| JP | 2007-065161 A | 3/2007 | |
| JP | 2007-099741 A | 4/2007 | |
| JP | 2007-163846 A | 6/2007 | |
| JP | 2007-171895 A | 7/2007 | |
| JP | 2007-199653 A | 8/2007 | |
| JP | 2007-226170 A | 9/2007 | |
| JP | 2007-226204 A | 9/2007 | |
| JP | 2007-316282 A | 12/2007 | |
| JP | 2008-026600 A | 2/2008 | |
| JP | 2008-096684 A | 4/2008 | |
| JP | 2008-111103 A | 5/2008 | |
| JP | 2008-158002 A | 7/2008 | |
| JP | WO2010041626 * | 4/2010 | ................ G03F 7/11 |
| JP | 2010271654 * | 12/2010 | ................ G03F 7/11 |
| WO | 2004-066377 A1 | 8/2004 | |

OTHER PUBLICATIONS

J. Hatakeyama et al., Investigation of Discrimination Enhancement in Polysilsesquioxane Based Positive Resist for ArF Lithography:, SPIE vol. 3333, 1998, pp. 62-72.

U. Schaedeli et al., "Evaluation of Materials for 193-nm Lithography", Journal of Photopolymer Science and Technology, vol. 9, No. 3, 1996, pp. 435-446.

R. Kwong et al., IBM 193nm bilayer Resist: materials, Lithographic Performance and Optimization, SPIE vol. 4345, 2001, pp. 57.

J. M. Moran and D. Maydan, "High resolution, steep profile resist patterns", J. Va. Sci. Technolo., vol. 16, No. 6, 1979, pp. 1620-1624.

Donald W. Johnson, "Thermolysis of Positive Photoresists", SPIE, vol. 469, 1984, pp. 72-79.

T. Noda et al., "A Comment on the Structure of Glassy Carbon", Glass Carbon Bull. Chem. Soc. JPN., vol. 41, No. 12, 1968, pp. 3023-3024.

Abe et al., "Sub-55-nm Etch Process Using Stacked-Mask Process", Proc. of Symp. Dry. Process, 2005, pp. 11-12.

T. Lynch et al., "Properties and Performance of Near UV Reflectivity Control Layers", SPIE vol. 2195, 1994, pp. 225-229.

\* cited by examiner

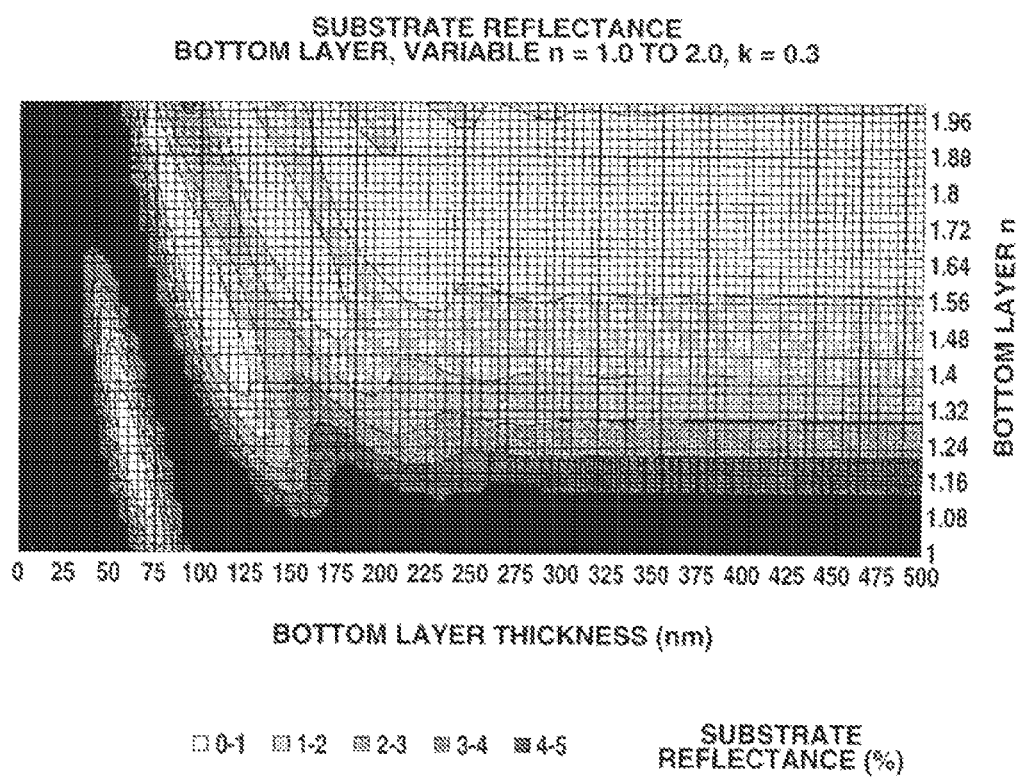

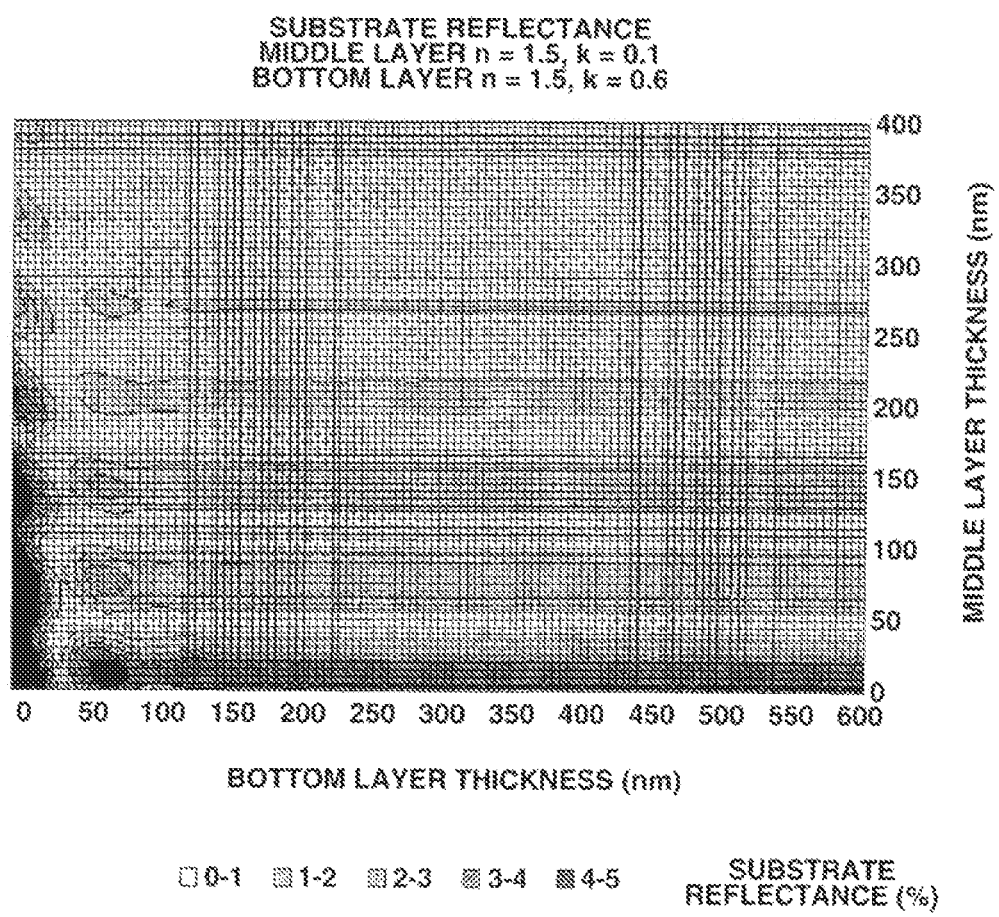

NAPHTHALENE DERIVATIVE, RESIST BOTTOM LAYER MATERIAL, RESIST BOTTOM LAYER FORMING METHOD, AND PATTERNING PROCESS

CROSS-REFERENCE TO RELATED APPLICATION

This non-provisional application claims priority under 35 U.S.C. §119(a) on Patent Application No. 2010-140533 filed in Japan on Jun. 21, 2010, the entire contents of which are hereby incorporated by reference.

TECHNICAL FIELD

This invention relates to a resist bottom layer material for forming a resist bottom layer useful as an antireflective coating (ARC) in the multilayer resist process used in micropatterning for the fabrication of semiconductor devices or the like, a method for forming a resist bottom layer, and a pattern forming process adapted for the lithography including exposure to KrF excimer laser (248 nm), ArF excimer laser (193 nm), $F_2$ laser (157 nm), $Kr_2$ laser (146 nm), $Ar_2$ laser (126 nm), soft X-ray or EUV (13.5 nm), electron beam, or X-ray, using the resist bottom layer material.

BACKGROUND ART

While a number of recent efforts are being made to achieve a finer pattern rule in the drive for higher integration and operating speeds in LSI devices, the commonly used light exposure lithography is approaching the essential limit of resolution determined by the light source wavelength.

As the light source used in the lithography for resist pattern formation, g-line (436 nm) or i-line (365 nm) from a mercury lamp has been widely used. One means believed effective for further reducing the feature size is to reduce the wavelength of exposure light. For the mass production process of 64 M-bit DRAM, the exposure light, source of i-line (365 nm) was replaced by a KrF excimer laser having a shorter wavelength of 248 nm. However, for the fabrication of DRAM with a degree of integration of 1 G or more requiring a finer patterning technology (processing feature size 0.13 µm or less), a shorter wavelength light source is required. In particular, photolithography using ArF excimer laser light (193 nm) is now under investigation.

On the other hand, it is known in the art that the bilayer resist process is advantageous in forming a high-aspect ratio pattern on a stepped substrate. In order that a bilayer resist film be developable with a common alkaline developer, high molecular weight silicone compounds having hydrophilic groups such as hydroxyl and carboxyl groups must be used.

Among silicone base chemically amplified positive resist compositions, recently proposed were those compositions for KrF excimer laser exposure comprising a base resin in the form of polyhydroxybenzylsilsesquioxane, which is a stable alkali-soluble silicone polymer, in which some phenolic hydroxyl groups are protected with t-BOC groups, in combination with an acid generator (see JP-A H06-118651 and SPIE vol. 1925 (1993), 077). For ArF excimer laser exposure, positive resist compositions comprising as a base a silsesquioxane of the type in which cyclohexylcarboxylic acid has substituted thereon an acid labile group were proposed (see JP-A H10-324748, JP-A H11-302382, and SPIE vol. 3333 (1998), p 62). For $F_2$ laser exposure, positive resist compositions based on a silsesquioxane having hexafluoroisopropanol as a dissolvable group were proposed (see JP-A 2002-55456). The above polymer bears in its backbone a polysilsesquioxane containing a ladder skeleton produced through polycondensation of a trialkoxysilane or trihalosilane.

Silicon-containing (meth)acrylate polymers were proposed as a resist base polymer having silicon pendants on side chains (see JP-A H09-110938, J. Photopolymer Sci. and Technol., Vol. 9, No. 3 (1996), p 435-446).

The lower (or bottom) layer of the bilayer resist process is formed of a hydrocarbon compound which can be etched with oxygen gas, and must have high etch resistance since it serves as a mask when the underlying substrate is subsequently etched. For oxygen gas etching, the bottom layer must be formed solely of a silicon atom-free hydrocarbon. To improve the line-width controllability of the upper (or top) layer of silicon-containing resist and to minimize the sidewall corrugation and pattern collapse by standing waves, the bottom layer must also have the function of an antireflective coating (ARC). Specifically, the reflectance from the resist bottom layer back into the resist top layer must be reduced to or below 1%.

Now, the results of calculation of reflectance at film thickness varying up to the maximum of 500 nm are shown in FIGS. 2 and 3. Assume that the exposure wavelength is 193 nm, and the resist top layer has an n value of 1.74 and a k value of 0.02. FIG. 2 shows substrate reflectance when the resist bottom layer has a fixed k value of 0.3, the n value varies from 1.0 to 2.0 on the ordinate and the film thickness varies from 0 to 500 nm on the abscissa. Assuming that the resist bottom layer of the bilayer resist process has a thickness of 300 nm or greater, optimum values at which the reflectance is reduced to or below 1% exist in the refractive index (n) range of 1.6 to 1.9 which is approximate to or slightly higher than that of the resist top layer.

FIG. 3 shows substrate reflectance when the resist bottom layer has a fixed n value of 1.5 and the k value varies from 0 to 0.8. Assuming that the resist bottom layer of the bilayer resist process has a thickness of at least 300 nm, the reflectance can be reduced to or below 1% as long as the k value is in a range of 0.24 to 0.15. By contrast, the antireflective coating used in the form of a thin film of about 40 nm thick in the single-layer resist process has an optimum k value in the range of 0.4 to 0.5, which differs from the optimum k value of the resist bottom layer used with a thickness of 300 nm or greater in the bilayer resist process. For the resist bottom layer in the bilayer resist process, a film having a lower k value, that is, more transparent is necessary.

As the material for forming a resist bottom layer in 193 nm lithography, copolymers of polyhydroxystyrene with acrylates are under study as described in SPIE Vol. 4345 (2001) p 50. Polyhydroxystyrene has a very strong absorption at 193 nm and its k value is as high as around 0.6 by itself. By copolymerizing it with an acrylic compound having a k value of almost 0, the k value of the copolymer is adjusted to around 0.25.

However, the resistance of the acrylic polymer to substrate etching is weak as compared with polyhydroxystyrene, and a considerable proportion of the acrylic compound must be copolymerized in order to reduce the k value. As a result, the resistance to substrate etching is considerably reduced. The etch resistance is not only reflected by the etching speed, but also evidenced by the development of surface roughness after etching. Through copolymerization of acrylic compound, the surface roughness after etching is increased to a level of serious concern.

Also proposed was a tri-layer process of stacking a resist top layer of a silicon-free single-layer resist film, a resist middle layer containing silicon below the top layer, and a resist bottom layer of organic film below the middle layer. See J. Vac. Sci. Technol., 16(6), November/December 1979. Since the single-layer resist generally provides better resolution than the silicon-bearing resist, the tri-layer process permits such a high resolution single-layer resist to be used as an imaging layer for light exposure. A spin-on-glass (SOG) coating is used as the resist middle layer. A number of SOG films have been proposed.

In the trilayer process, the optimum optical constants of the bottom layer for controlling reflection from the substrate are different from those in the bilayer process. The purpose of minimizing substrate reflection, specifically to a level of 1% or less is the same between the bi- and tri-layer processes. In the bilayer process, only the resist bottom layer is endowed with the antireflective effect. In the tri-layer process, either one or both of the resist middle layer and resist bottom layer may be endowed with the antireflective effect.

U.S. Pat. No. 6,506,497 and U.S. Pat. No. 6,420,088 disclose silicon-containing layer materials endowed with antireflective effect. In general, a multi-layer antireflective coating has greater antireflective effect than a single-layer antireflective coating and is commercially widely used as an antireflective film for optical articles. A higher antireflective effect is obtainable by imparting an antireflective effect to both a resist middle layer and a resist bottom layer. If the silicon-containing resist middle layer in the trilayer process is endowed with the function of ARC, the resist bottom layer need not necessarily possess the maximum function of ARC as in the case of the bilayer process. In the trilayer process, the resist bottom layer is required to have high etch resistance during substrate processing rather than the ARC function. Then a novolac resin containing more aromatic groups and having high etch resistance has been used as the resist bottom layer in the trilayer process.

FIG. 4 illustrates substrate reflectance with a change of the k value of the resist middle layer. It is seen that by setting a k value as low as 0.2 or less and an appropriate thickness to the resist middle layer, a satisfactory antireflective effect as demonstrated by a substrate reflectance of up to 1% is achievable. In general, the ARC film must have a k value of 0.2 or greater in order to reduce reflectance to or below 1% at a film thickness of 100 nm or less (see FIG. 3). In the trilayer resist structure wherein the resist bottom layer serves to restrain reflection to a certain extent, the resist middle layer may have an optimum k value of less than 0.2.

FIGS. 5 and 6 illustrate changes of reflectance with the varying thickness of the resist middle layer and resist bottom layer, when the resist bottom layer has a k value of 0.2 and 0.6, respectively. The resist bottom layer in FIG. 5 has a k value of 0.2 which assumedly corresponds to the resist bottom layer optimized for the bilayer process, and the resist bottom layer in FIG. 6 has a k value of 0.6 which is approximate to the k values at 193 nm of novolac and polyhydroxystyrene. The thickness of the resist bottom layer varies with the topography of the substrate whereas the thickness of the resist middle layer is kept substantially unchanged so that presumably it can be coated to the predetermined thickness.

The resist bottom layer with a higher k value (0.6) is effective in reducing reflectance to 1% or less with a thinner film. In the event that the resist bottom layer has a k value of 0.2 and a thickness of 250 nm, the resist middle layer must be increased in thickness in order to provide a reflectance of 1% or less. Increasing the thickness of the resist middle layer is not preferable because a greater load is applied to the resist film as the uppermost layer during dry etching of the resist middle layer.

FIGS. 5 and 6 illustrate reflection during dry exposure through an exposure tool having a lens with a NA of 0.85, indicating that by optimizing the n and k values and thickness of the resist middle layer for the trilayer process, a reflectance of up to 1% is achievable independent of the k value of the resist bottom layer. Nevertheless, with the advance of the immersion lithography, the NA of the projection lens increases beyond 1.0, and the angles of light entering not only the resist film, but also the underlying ARC film become smaller. The ARC film serves to control reflection due to the absorption of the film itself and the offsetting effect by optical interference. Since oblique light produces a less optical interference effect, reflection increases. Of the films in the trilayer process, it is the resist middle layer that provides reflection control by utilizing the optical interference effect. The resist bottom layer is too thick to utilize the optical interference effect and lacks the anti-reflective function due to the offsetting effect by optical interference. It is necessary to control the reflection from the surface of the resist bottom layer. To this end, the resist bottom layer must have a k value of less than 0.6 and an n value approximate to that of the overlying, resist middle layer. If a film has a too small value of k and too high transparency, reflection from the substrate also occurs, and a k value of about 0.25 to 0.48 is optimum in the case of immersion lithography at NA 1.3. With respect to the n value, a value approximate to the resist's n value of 1.7 is the target for both the middle and bottom layers.

Since benzene ring structure has very strong absorption, cresol novolac resins and polyhydroxystyrene resins containing the same have k values in excess of 0.6. Naphthalene ring structure is one of structures having higher transparency at wavelength 193 nm and higher etch resistance than the benzene ring. For example, JP-A 2002-014474 discloses a resist bottom layer comprising a naphthalene or anthracene ring. According to the inventors' measurements, naphthol co-condensed novolac resin and polyvinylnaphthalene resin have a k value between 0.3 and 0.4. Also the naphthol co-condensed novolac resin and polyvinylnaphthalene resin have a low n value at wavelength 193 nm, specifically, the n value is 1.4 for the naphthol co-condensed novolac resin and as low as 1.2 for the polyvinylnaphthalene resin. Acenaphthylene polymers disclosed in JP-A 2001-040293 and JP-A 2002-214777, for example, have a n value of 1.5 and a k value of 0.4 at 193 nm, close to the target values. There is a need for a bottom layer having a high n value, a low k value, transparency and high etch resistance. Notably JP-A 2007-199653 discloses a resist bottom layer material having a bisnaphthol group, the material having n and k values close to the target values, and improved etch resistance.

If the underlying processable substrate has steps, it is necessary to deposit a resist bottom layer to planarize the steps. By the planarization of the resist bottom layer, a variation in thickness of an overlying film, which may be a resist middle layer or a resist top layer or photoresist film, is minimized, and the focus margin of lithography can be enlarged.

When an amorphous carbon bottom layer is formed by CVD using a reactant gas such as methane, ethane or acetylene gas, it is difficult to bury steps to be flat. On the other hand, when a resist bottom layer is formed by spin coating, there is a benefit that irregularities on the substrate can be buried. Suitable means for improving the burying properties of a material of coating type include the use of a novolac resin having a low molecular weight and a broad molecular weight distribution as disclosed in JP-A 2002-047430 and a blend of a base polymer and a low molecular weight compound having a low melting point as disclosed in JP-A H11-154638.

It is known from SPIE vol. 469, p 72 (1984) that novolac resins cure through intermolecular crosslinking merely by heating. Reported therein is a crosslinking mechanism by radical coupling that upon heating, a phenoxy radical generates from a phenolic hydroxyl group of cresol novolac resin, and the radical migrates to methylene, a linking group of the novolac resin via resonance, whereby methylene moieties crosslink together. JP 3504247 discloses a pattern forming process using a bottom layer having a carbon density which is increased by thermally induced dehydrogenation or dehydration condensation reaction of polycyclic aromatic compounds such as polyarylene, naphthol novolac, and hydroxyanthracene novolac.

A vitreous carbon film is formed by heating at or above 800° C. (see Glass Carbon Bull. Chem. Soc. JPN, 41 (12) 3023-3024 (1968)). However, the upper limit of the temperature to which the wafer can be heated by the lithography wafer process is up to 600° C., preferably up to 500° C. when thermal impacts like device damage and wafer deformation are taken into account.

It is reported in Proc. of Symp. Dry. Process, p 11 (2005) that as the processing line width is reduced, the resist bottom layer can be twisted or bowed when the processable substrate is etched using the resist bottom layer as mask. During etching of the substrate with fluorocarbon-based gas, a phenomenon occurs that hydrogen atoms in the resist bottom layer are replaced by fluorine atoms. As the surface of the resist bottom layer is converted to fluorocarbon-like, the bottom layer increases its volume so that it may swell or lower its glass transition temperature, allowing a finer pattern to be twisted. It is described in the literature that twisting can be prevented by applying a resist bottom layer having a low hydrogen content. An amorphous carbon film formed by CVD is effective for preventing twist because the hydrogen content of the film can be minimized. However, the CVD has poor step burying properties as pointed out above, and the CVD apparatus may be difficult to introduce because of its price and footprint area. If the twist problem can be solved by a bottom layer material from which a film can be formed by coating, specifically spin coating, significant merits would result from simplification of process and apparatus.

Also under study is a multilayer process in which a hard mask is formed on the resist bottom layer by the CVD technique. In the case of silicon-based hard masks (such as silicon oxide, silicon nitride, and silicon oxynitride films) as well, inorganic hard masks formed by CVD or similar deposition techniques have more etch resistance than hard masks formed by the spin coating technique. In the event the processable substrate is a low-dielectric-constant film, the photoresist may be poisoned therefrom (poisoning problem). The CVD film is more effective as a barrier film for preventing the poisoning problem.

Then a process involving forming a resist bottom layer by spin coating for planarization purpose, and forming an inorganic hard mask middle layer as the resist middle layer by a CVD technique is investigated. When an inorganic hard mask middle layer, especially a nitride film, is formed by a CVD technique, the substrate must be heated at a temperature of at least 300° C., typically about 400° C. Accordingly, when the resist bottom layer is formed by spin coating, the substrate must have heat resistance at 400° C. Ordinary cresol novolac resins, naphthol novolac resins, and even fluorene bisphenol resins known to be heat resistant fail to withstand heat at 400° C., experiencing a substantial film slimming after heating. There is a need for a resist bottom layer which can withstand heating at high temperature when an inorganic hard mask middle layer is formed by a CVD technique.

Because of the problem of film slimming or resin degradation after heating due to shortage of heat resistance, heat treatment of a resist bottom layer material is usually carried out at or below 300° C., typically 80 to 300° C. The heat treated film, however, still suffers from slimming after solvent treatment or twisting of the pattern during etching of the substrate.

As discussed above, it would be desirable to have a method for forming a resist bottom layer which has optimum values of n and k as the ARC film, burying properties, etching resistance, and solvent resistance, and has sufficient heat resistance to withstand high temperature encountered during formation of an inorganic hard mask middle layer by a CVD or similar deposition technique, and prevents pattern twisting during substrate etching.

CITATION LIST

Patent Document 1: JP-A H06-118651
Patent Document 2: JP-A H10-324748
Patent Document 3: JP-A H11-302382
Patent Document 4: JP-A 2002-055456
Patent Document 5: JP-A H09-110938
Patent Document 6: U.S. Pat. No. 6,506,497
Patent Document 7: U.S. Pat. No. 6,420,088
Patent Document 8: JP-A 2002-014474
Patent Document 9: JP-A 2001-040293
Patent Document 10: JP-A 2002-214777
Patent Document 11: JP-A 2007-199653
Patent Document 12: JP-A 2002-047430
Patent Document 13: JP-A H11-154638
Patent Document 14: JP 3504247
Non-Patent Document 1: SPIE Vol. 1925 (1993) p 377
Non-Patent Document 2: SPIE Vol. 3333 (1998) p 62
Non-Patent Document 3: Photopolymer Sci. and Technol. Vol. 9, No. 3 (1996) p 435-446
Non-Patent Document 4: SPIE Vol. 4345 (2001) p 50
Non-Patent Document 5: J. Vac. Sci. Technol., 16(6), November/December 1979
Non-Patent Document 6: SPIE Vol. 469 (1984) p 72
Non-Patent Document 7: Glass Carbon Bull. Chem. Soc. JPN. 41 (12) 3023-3024 (1968)
Non-Patent Document 8: Proc. of Symp. Dry. Process, 2005, p 11

SUMMARY OF INVENTION

An object of the present invention is to provide a naphthalene derivative; an resist bottom layer material comprising the naphthalene derivative and useful to form a resist bottom layer in a multilayer resist film of at least three layers used in the lithography, the resist bottom layer being capable of reducing reflectance, having etch resistance, heat resistance, and solvent resistance, and being devoid of twist during etching of an underlying substrate; a method for forming a resist bottom layer using the same; and a pattern-forming process using the same.

In one aspect, the invention provides a naphthalene derivative having the general formula (1).

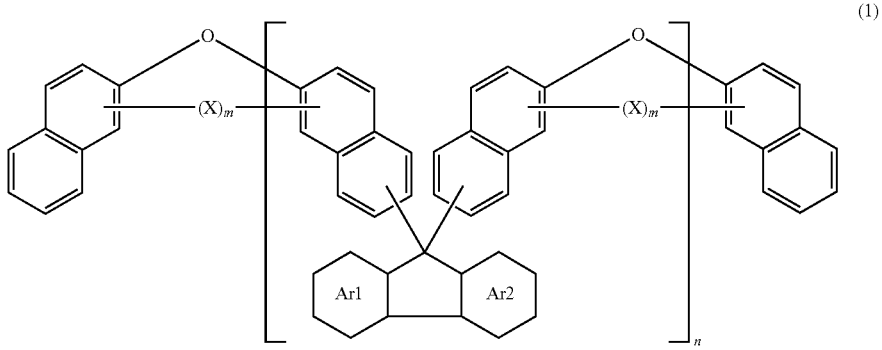

Herein cyclic structures Ar1 and Ar2 denote a benzene or naphthalene ring, X is a single bond or $C_1$-$C_{20}$ alkylene, m is 0 or 1, and n is such a natural number as to provide a molecular weight of up to 100,000.

In another aspect, the invention provides a naphthalene derivative comprising a partial structure having the general formula (2).

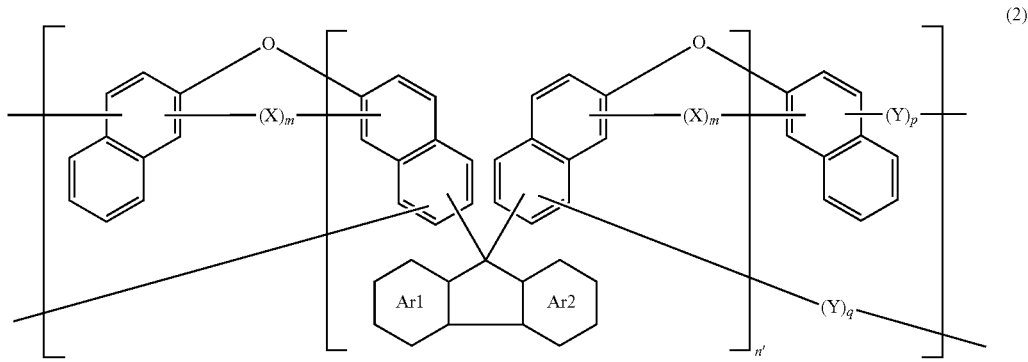

Herein cyclic structures Ar1 and Ar2 denote a benzene or naphthalene ring, X is a single bond or $C_1$-$C_{20}$ alkylene, m is 0 or 1, Y is a single bond or $C_1$-$C_{20}$ alkylene, p and q each are 0 or a natural number, with the proviso that p and q are not equal to 0 at the same time, and n' is such a natural number as to provide a molecular weight of up to 200,000.

In a third aspect, the invention provides a resist bottom layer material comprising a naphthalene derivative having formula (1) or (2), or a polymer comprising the naphthalene derivative.

In a fourth aspect, the invention provides a method for forming a resist bottom layer which is included in a multilayer resist film of at least three layers used in the lithography, comprising the steps of coating a resist bottom layer material comprising a naphthalene derivative having formula (1) or (2) or a polymer comprising the naphthalene derivative and optionally an organic solvent, a crosslinker and an acid generator onto a substrate, typically by a spin coating technique, and heat treating the coating of resist bottom layer material at a temperature of more than 150° C. to 600° C. for 10 to 600 seconds for curing.

In a fifth aspect, the invention provides a process for forming a pattern in a substrate by lithography, comprising at least the steps of forming a resist bottom layer on a substrate by the above method, forming a resist middle layer on the resist bottom layer using a silicon-containing resist middle layer material, forming a resist top layer on the resist middle layer using a resist top layer material which is a photoresist composition, exposing a pattern circuit region of the resist top layer to radiation, developing the resist top layer with a developer to form a resist pattern therein, etching the resist middle layer using the resist pattern as an etching mask, etching the resist bottom layer using the resulting resist middle layer pattern as an etching mask, and etching the substrate using the resulting resist bottom layer pattern as an etching mask.

In a sixth aspect, the invention provides a process for forming a pattern in a substrate by lithography, comprising at least the steps of forming a resist bottom layer on a substrate by the above method, forming on the resist bottom layer an inorganic hard mask middle layer which is selected from a silicon oxide film, silicon nitride film, and silicon oxynitride film, forming a resist top layer on the inorganic hard mask middle layer using a resist top layer material which is a photoresist composition, exposing a pattern circuit region of the resist top layer to radiation, developing the resist top layer with a developer to form a resist pattern therein, etching the inorganic hard mask middle layer using the resist pattern as an etching mask, etching the resist bottom layer using the resulting inorganic hard mask middle layer pattern as an etching mask, and etching the substrate using the resulting resist bottom layer pattern as an etching mask.

In a seventh aspect, the invention provides a process for forming a pattern in a substrate by lithography, comprising at least the steps of forming a resist bottom layer on a substrate by the above method, forming on the resist bottom layer an inorganic hard mask middle layer which is selected from a silicon oxide film, silicon nitride film, and silicon oxynitride film, forming an organic ARC film on the inorganic hard mask middle layer, forming a resist top layer on the organic ARC film using a resist top layer material which is a photoresist composition, exposing a pattern circuit region of the resist top layer to radiation, developing the resist top layer with a developer to form a resist pattern therein, etching the organic ARC film and inorganic hard mask middle layer using the resist pattern as an etching mask, etching the resist bottom layer using the resulting inorganic hard mask middle layer pattern as an etching mask, and etching the substrate using the resulting resist bottom layer pattern as an etching mask.

Advantageous Effects of Invention

Since the method for forming a resist bottom layer which is included in a multilayer resist film of at least three layers used in the lithography uses a resist bottom layer material comprising a naphthalene derivative having formula (1) or (2) or a polymer comprising the naphthalene derivative, the resulting resist bottom layer has values of n and k optimum as ARC film, burying properties, improved etch resistance, high heat resistance and solvent resistance, capable of minimizing outgassing during bake, and being devoid of twist during etching of an underlying substrate through a line pattern having a high aspect ratio and a width of less than 60 nm. When an inorganic hard mask is formed by CVD on the resist bottom layer which has been formed by a spin coating technique, the resist bottom layer has sufficient heat resistance to withstand the temperature treatment for forming the inorganic hard mask middle layer. A pattern forming process in which the resist bottom layer formed by spin coating is combined with the inorganic hard mask formed by CVD is available.

BRIEF DESCRIPTION OF THE DRAWINGS

FIG. 2 is a graph plotting the substrate reflectance versus bottom layer thickness in bilayer process when the k value of the bottom layer is fixed at 0.3 and the n value varies from 1.0 to 2.0.

FIG. 6 is a graph plotting the substrate reflectance versus varying thickness of the bottom layer and middle layer in trilayer process when the bottom layer has a fixed n of 1.5 and a fixed k of 0.6, and the middle layer has a fixed n of 1.5 and a fixed k of 0.1.

Figure 1A:
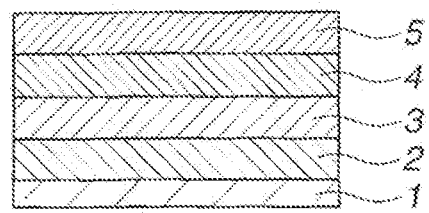
FIG. 1 illustrates a trilayer resist working process, FIGS. 1A through 1F showing steps of stacking and etching three layers.

It is noted that the definition of complex index of refraction includes a refractive index (n) and an extinction coefficient (k).

DESCRIPTION OF THE PREFERRED EMBODIMENTS

In the disclosure, the singular forms "a," "an" and "the" include plural referents unless the context clearly dictates otherwise. The notation (Cn-Cm) means a group containing from n to m carbon atoms per group.

The abbreviations and acronyms have the following meaning.

Mw: weight average molecular weight
Mn: number average molecular weight
Mw/Mn: molecular weight distribution or dispersity
GPC: gel permeation chromatography
PEB: post-exposure baking
ARC: antireflective coating
BARC: bottom antireflective coating It is understood that for some structures represented by chemical formulae, there can exist enantiomers and diastereomers because of the presence of asymmetric carbon atoms. In such a case, a single formula collectively represents all such isomers. The isomers may be used alone or in admixture.

Naphthalene Derivative

In one embodiment of the invention, a naphthalene derivative has the general formula (1).

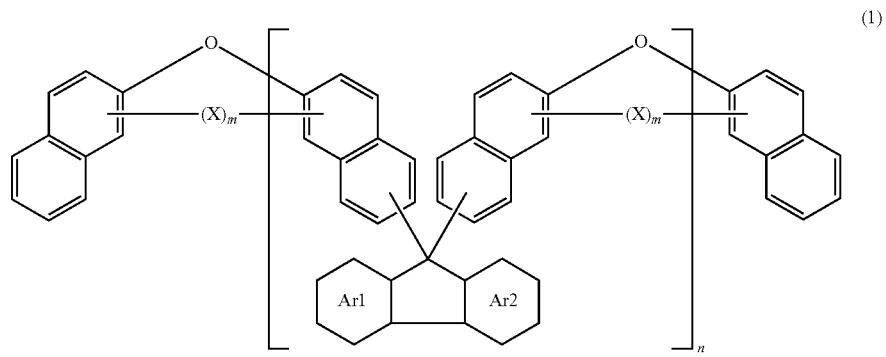

(1)

Herein cyclic structures Ar1 and Ar2 denote a benzene or naphthalene ring, X is a single bond or a $C_1$-$C_{20}$ alkylene group, m is 0 or 1, and n is such a natural number as to provide a molecular weight of up to 100,000.

Each of Ar1 and Ar2 denotes a benzene or naphthalene ring. Preferred examples of the partial structure:

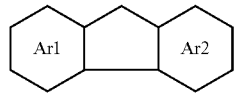

include the following partial structures.

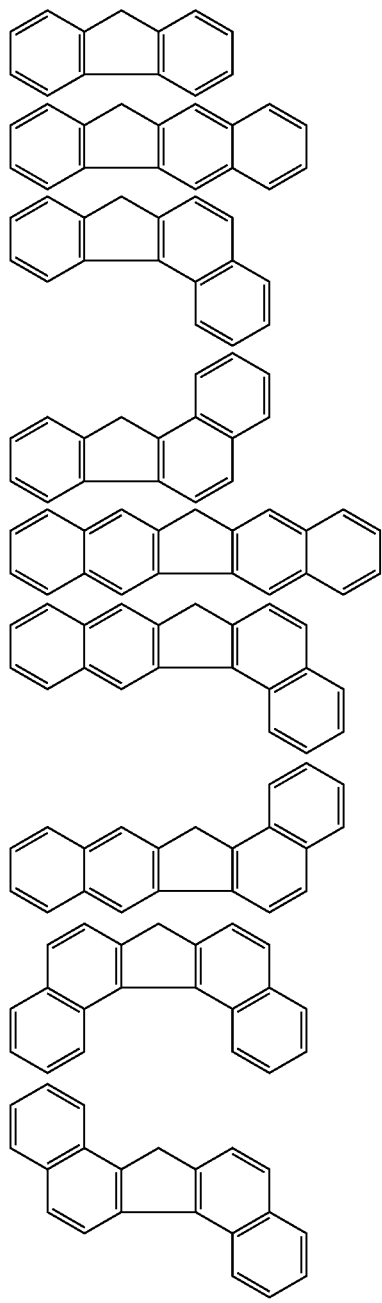

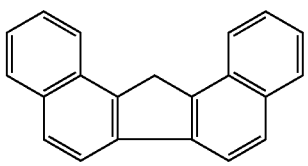

Inter alia, fluorene and benzofluorene ring structures are more preferred. In these groups, a hydrogen atom may be replaced by a halogen atom, hydrocarbon, hydroxyl, alkoxy, nitro, cyano group or the like.

X is a single bond or a $C_1$-$C_{20}$, preferably $C_1$-$C_{18}$, more preferably $C_1$-$C_{15}$ alkylene group. Specifically X is a single bond or CHR wherein R is hydrogen, a $C_1$-$C_{19}$ alkyl group or $C_5$-$C_{19}$ aryl group. The subscript m is 0 or 1. Specifically, preferred examples of the partial structure:

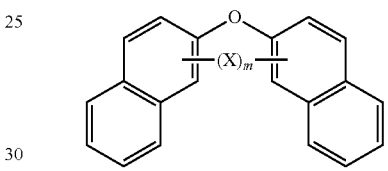

include the following partial structures.

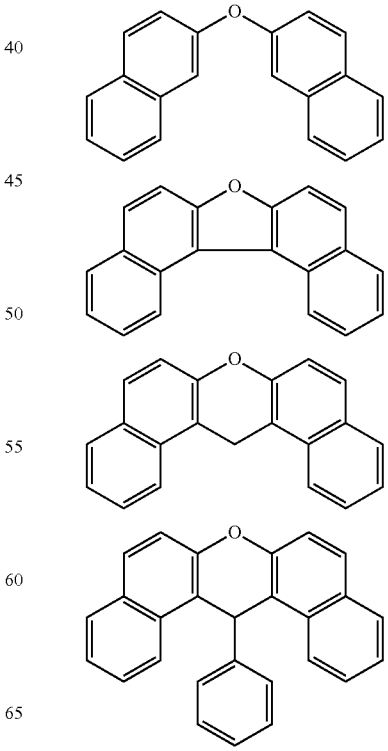

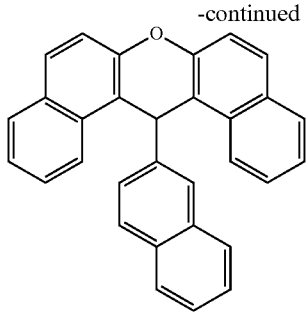
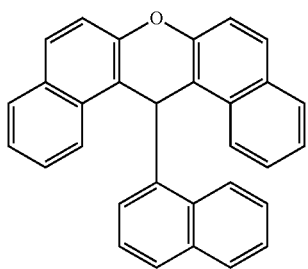
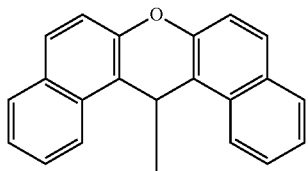
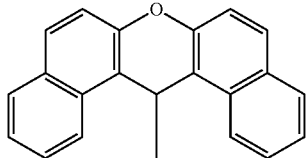
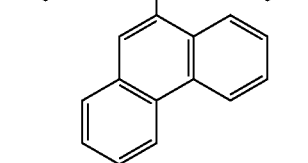

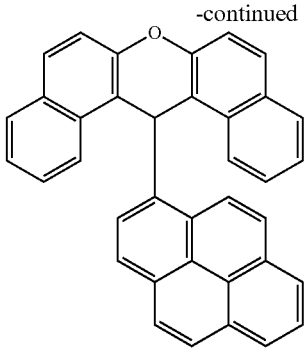
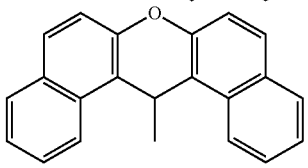
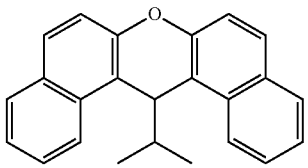
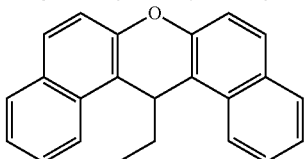
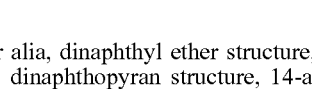

Inter alia, dinaphthyl ether structure, dinaphthofuran structure, dinaphthopyran structure, 14-alkyl-14-H-dibenzoxanthene structure, and 14-aryl-14-H-dibenzoxanthene structure are more preferred. In these groups, a hydrogen atom may be replaced by a halogen atom, hydrocarbon, hydroxyl, alkoxy, nitro, cyano group or the like.

The subscript n is such a natural number as to provide a molecular weight less than or equal to 100,000. As used herein, the term "molecular weight" is as measured by GPC versus polystyrene standards. Specifically n is such a natural number as to provide a weight average molecular weight (Mw) of less than or equal to 100,000, preferably 700 to 50,000, and more preferably 2,000 to 30,000.

The attachment site between the foregoing two partial structures is preferably the attachment site in the general formula below, though not limited thereto.

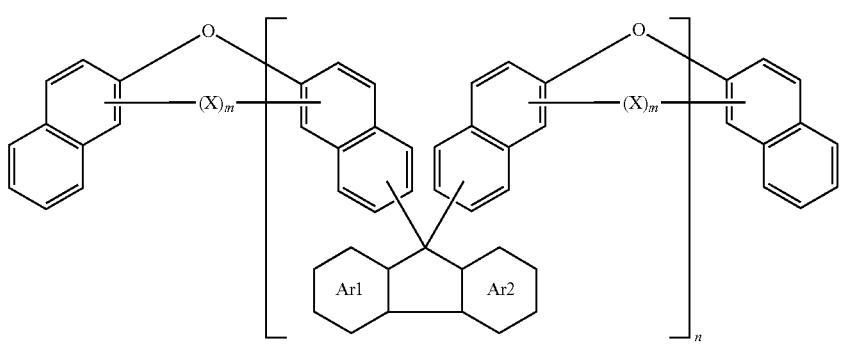

It is described how to prepare the naphthalene derivative having formula (1). One typical, non-limiting method is dehydration condensation reaction between a ketone compound (3) and a dinaphthyl ether compound (4), shown below. Preferably 1 to 20 moles, especially 1 to 5 moles of dinaphthyl ether compound (4) is used per mole of ketone compound (3).

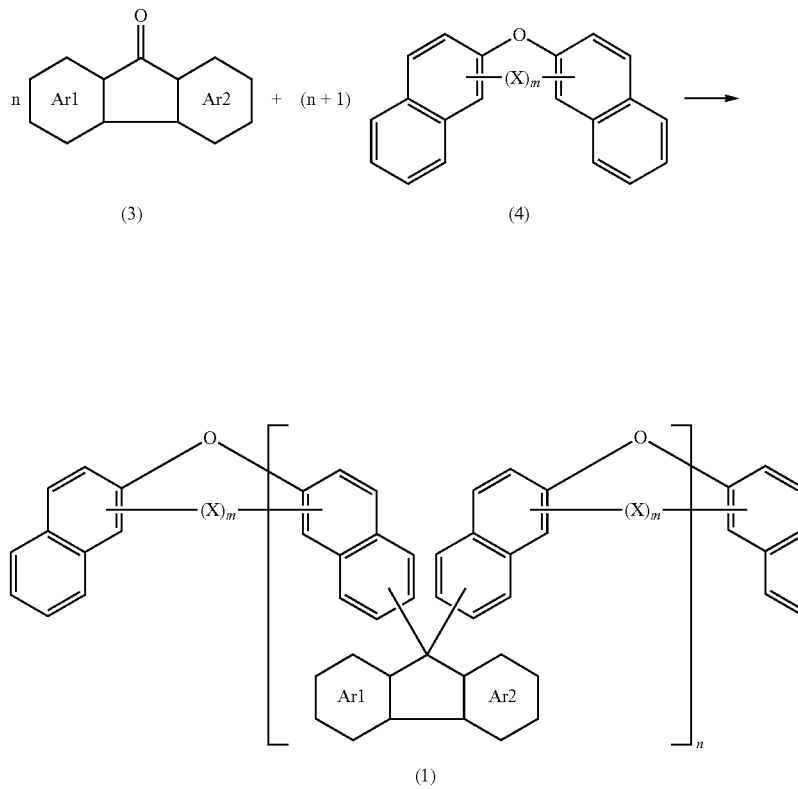

Usually the reaction may be conducted in a solventless system or in a solvent in the presence of an acid or base catalyst at room temperature or optionally under cooling or heating. Examples of the solvent used herein include alcohols such as methanol, ethanol, isopropyl alcohol, butanol, ethylene glycol, propylene glycol, diethylene glycol, glycerol, ethylene glycol monomethyl ether, and propylene glycol monomethyl ether; ethers such as diethyl ether, dibutyl ether, diethylene glycol diethyl ether, diethylene glycol dimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene; nitriles such as acetonitrile; ketones such as acetone, ethyl methyl ketone, and isobutyl methyl ketone; esters such as ethyl acetate, n-butyl acetate, and propylene glycol methyl ether acetate (PGMEA); and aprotic polar solvents such as dimethyl sulfoxide, N,N-dimethylformamide, and hexamethylphosphoric triamide, which may be used alone or in admixture of two or more. Examples of the acid catalyst used herein include mineral acids such as hydrochloric acid, hydrobromic acid, sulfuric acid, nitric acid, phosphoric acid, and heteropoly-acid; organic acids such as oxalic acid, trifluoroacetic acid, methanesulfonic acid, benzenesulfonic acid, p-toluenesulfonic acid, and trifluoromethanesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide. Examples of the base catalyst used herein include inorganic bases such as sodium hydroxide, potassium hydroxide, barium hydroxide, sodium carbonate, sodium hydrogen carbonate, potassium carbonate, lithium hydride, sodium hydride, potassium hydride, and calcium hydride; alkyl metals such as methyllithium, n-butyllithium, methylmagnesium chloride, and ethylmagnesium bromide; alkoxides such as sodium methoxide, sodium ethoxide, and potassium t-butoxide; and organic bases such as triethylamine, diisopropylethylamine, N,N-dimethylaniline, pyridine, and 4-dimethylaminopyridine. The reaction temperature is preferably from −50° C. to near the boiling point of the solvent, more preferably from room temperature to 100° C.

Described below is the design concept of the naphthalene derivative having formula (1). The naphthalene derivative having formula (1) is used to formulate a material for forming a resist bottom layer which is included in a multilayer resist film of at least three layers used in the lithography. As mentioned above, a film having a high carbon atom density and a low hydrogen atom density is necessary to establish the properties required for the resist bottom layer, including etch resistance, heat resistance, and anti-twisting during substrate etching. Then the bottom layer material should desirably have a high carbon atom density and a low hydrogen atom density.

One exemplary naphthalene derivative used in a resist bottom layer for comparison purposes is a 2-naphthol/fluorenone condensate having formula (5) below, also known as bisnaphthol fluorene (referred to as compound (5), hereinafter), as disclosed in JP-A 2007-99741. One known means for converting compound (5) into a high molecular weight compound is novolac formation. A novolac resin formed using formaldehyde is, for example, a resin comprising recurring units having formula (5') (referred to as resin (5'), hereinafter).

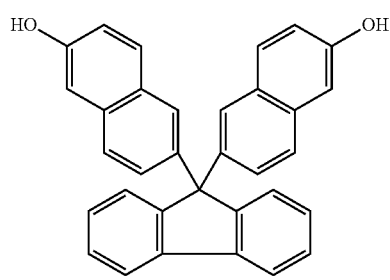
(5)

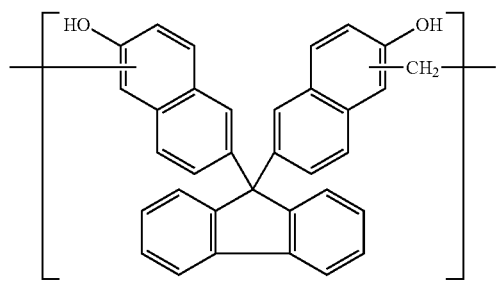
(5')

As compared with compound (5) or resin (5'), naphthalene derivative (1) of the invention has many structural advantages.
[1] Since the naphthalene derivative (1) has a structure that is obtained by eliminating water ($H_2O$) from the naphthol units of compound (5) to form an ether bond, the carbon density of the resin becomes higher by the value of water eliminated.
[2] Compound (5), which is a monomer, must be converted into a high molecular weight compound by novolac formation or suitable means before it can be used as a bottom layer material. The naphthalene derivative (1) is already a high molecular weight compound due to ether bonds and ready for use as a resin without a need for further polymerization such as novolac formation.

[3] While novolac form resin (5') has a reduced carbon density (or increased hydrogen density) due to novolac crosslink —$CH_2$—, naphthalene derivative (1) is free of such disadvantage.

[4] If necessary, intermolecular crosslinks may be introduced into naphthalene derivative (1) by novolac formation or suitable means.

Improved properties of the bottom layer film attributable to these advantages [1] to [4] will be demonstrated in Examples.

On use of the naphthalene derivative having formula (1) as a resist bottom layer material, if desired, the naphthalene derivative (1) may be converted to a higher molecular weight compound, that is, a naphthalene derivative comprising a partial structure having the general formula (2).

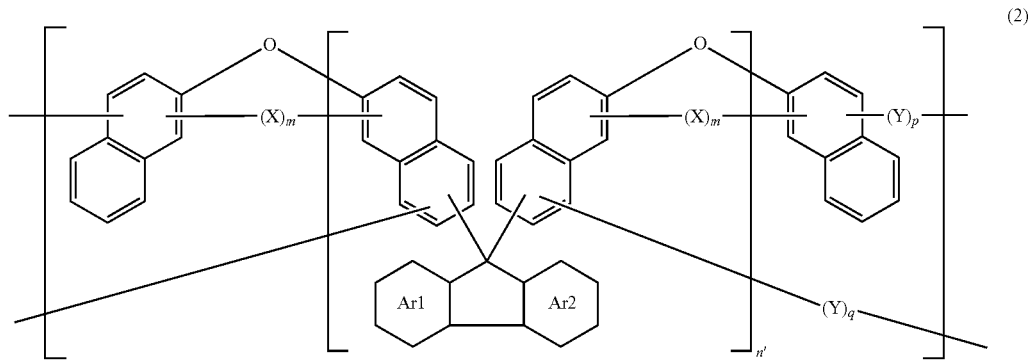
(2)

Herein Ar1, Ar2, X and m are as defined above. Y is a single bond or preferably $C_1$-$C_{20}$, $C_1$-$C_{15}$ alkylene, p and q each are 0 or a natural number, with the proviso that p and q are not equal to 0 at the same time, and n' is such a natural number as to provide a molecular weight of up to 200,000.

One exemplary means for converting naphthalene derivative (1) to a higher molecular weight compound is novolac formation through condensation with another component, which is described below. The novolac forming reaction corresponds to formula (2) wherein Y is $C_1$-$C_{20}$ alkylene. The novolac forming reaction uses an aldehyde, examples of which include formaldehyde, trioxan, paraformaldehyde, acetaldehyde, benzaldehyde, propionaldehyde, phenylacetaldehyde, α-phenylpropionaldehyde, β-phenylpropionaldehyde, 1-naphthaldehyde, 2-naphthaldehyde, and furfural. These aldehyde compounds may be substituted with one or more halogen atom, hydrocarbon, hydroxyl, alkoxy, nitro, cyano group or the like. Of these, formaldehyde and equivalents, benzaldehyde, 1-naphthaldehyde, 2-naphthaldehyde, and substituted forms of the foregoing are preferred. These aldehyde compounds may be used alone or in admixture of two or more. The aldehyde compound is preferably used in an amount of 0.2 to 5 moles, more preferably 0.5 to 2 moles per mole of the naphthalene derivative (1).

The novolac forming reaction may be effected in the presence of a catalyst. Acid catalysts are preferred. Examples of the acid catalyst used herein include mineral acids such as hydrochloric acid, hydrobromic acid, sulfuric acid, nitric acid, phosphoric acid, and heteropoly-acid; organic acids such as oxalic acid, trifluoroacetic acid, methanesulfonic acid, benzenesulfonic acid, p-toluenesulfonic acid, and trifluoromethanesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide. Inter alia, acidic catalysts such as hydrochloric acid, sulfuric acid, nitric acid, formic acid, oxalic acid, acetic acid, methanesulfonic acid, camphorsulfonic acid, tosylic acid, and trifluoromethanesulfonic acid are preferred. The acidic catalyst is typically used in an amount of $1\times10^{-5}$ to $5\times10^{-1}$ mole per mole of the naphthalene derivative (1). Reaction may be conducted by charging naphthalene derivative (1), aldehyde compound and catalyst all at once, or by adding dropwise any selected component. At the end of reaction, the unreacted reactants, catalyst and the like are removed from the reaction system. To this end, the reactor may be heated to a temperature of 130 to 230° C. under a vacuum of 1 to 50 mmHg for removing any volatiles.

Upon novolac forming reaction of the naphthalene derivative (1), another phenol compound may be co-present for copolymerization. Examples of the phenol which can be copolymerized include phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-t-butylphenol, 3-t-butylphenol, 4-t-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-t-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-t-butyl-5-methylphenol, pyrogallol, thymol, isothymol, 1-naphthol, 2-naphthol, 2-methyl-1-naphthol, 4-methoxy-1-naphthol, 7-methoxy-2-naphthol, 1,5-dihydroxynaphthalene, 1,7-dihydroxynaphthalene, 2,6-dihydroxynaphthalene, methyl 3-hydroxynaphthalene-2-carboxylate, 4-tritylphenol, hydroxyanthracene, dihydroxyanthracene, trihydroxyanthracene, hydroxypyrene, bisphenol, and trisphenol. These compounds may be substituted with one or more halogen atom, hydrocarbon, hydroxyl, alkoxy, nitro, cyano group or the like.

Also the naphthalene derivative (1) may be subjected to polycondensation with a polycondensable monomer to form a polymer, which may be used as the resist bottom layer material. Suitable monomers include indene, hydroxyindene, benzofuran, acenaphthylene, biphenyl, dicyclopentadiene, tetrahydroindene, 4-vinylcyclohexene, norbornadiene, 5-vinylnorborn-2-ene, α-pinene, β-pinene, and limonene. These monomers may be substituted with one or more halogen atom, hydrocarbon, hydroxyl, alkoxy, nitro, cyano group or the like. Also included are copolymers of three or more components. The other phenol compound or the polycondensable monomer is preferably used in an amount of more than 0% to 50% by weight based on the weight of the naphthalene derivative.

The novolac resin or polycondensed resin preferably has a weight average molecular weight (Mw) of 1,000 to 200,000, more preferably 2,000 to 50,000, as measured versus polystyrene standards, and a dispersity (Mw/Mn) in the range of 1.2 to 7. It is preferred that the molecular weight distribution of the resin is narrowed by cutting off the monomeric and oligomeric components and low-molecular weight fractions having a Mw of up to 1,000, because the crosslinking efficiency is increased and the content of volatile components during bake is minimized to prevent contamination around the bake cup.

Another exemplary means for converting the naphthalene derivative (1) into a high molecular weight compound is oxidative coupling by dehydrogenation. Oxidative coupling reaction corresponds to formula (2) wherein Y is a single bond. The oxidative coupling reaction is conducted by heating at a temperature of 80 to 500° C. in air or in the presence of oxygen. Metal salts and complexes may be used as the catalyst or reagent for the reaction, while examples include lead tetracetate, diacetoxyiodobenzene, vanadium oxychloride, vanadium oxyfluoride, iron(III) chloride, iron(III) perchlorate, potassium hexacyanoferrate(III), ruthenium oxide, cobalt fluoride, thallium trifluoroacetate, copper(II) chloride, and di-µ-hydroxo-[(N,N,N',N'-tetramethyl-ethylenediamine)copper(II) chloride. Oxidative coupling may be used as the means for previously converting the naphthalene derivative (1) into a high molecular weight compound. It is also possible to form a film while heating in air to drive oxidative coupling.

Also, a fused aromatic or alicyclic substituent group may be introduced into the naphthalene derivative having formula (1) or (2) or a polymer comprising the same. Examples of the substituent group which can be introduced herein are given below.

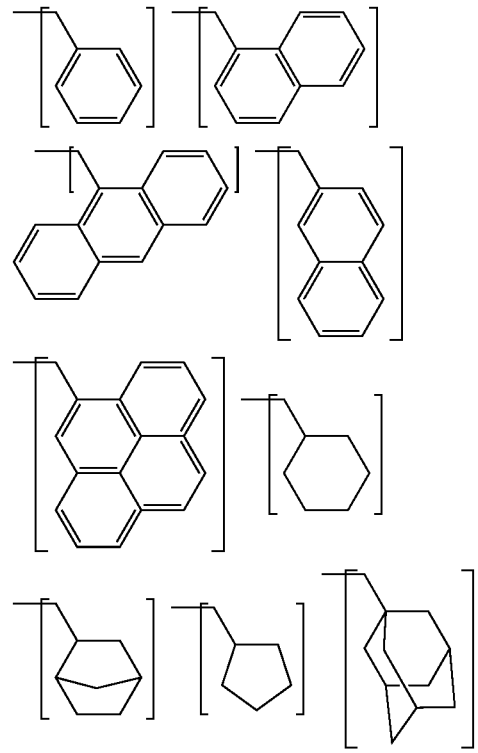

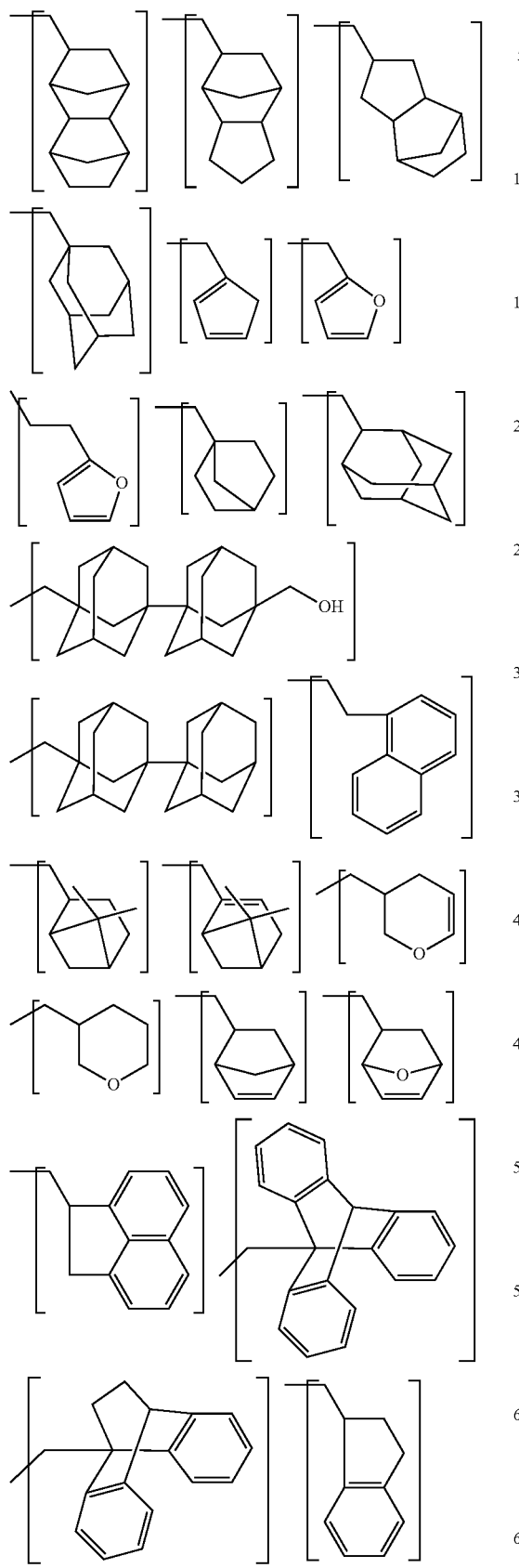
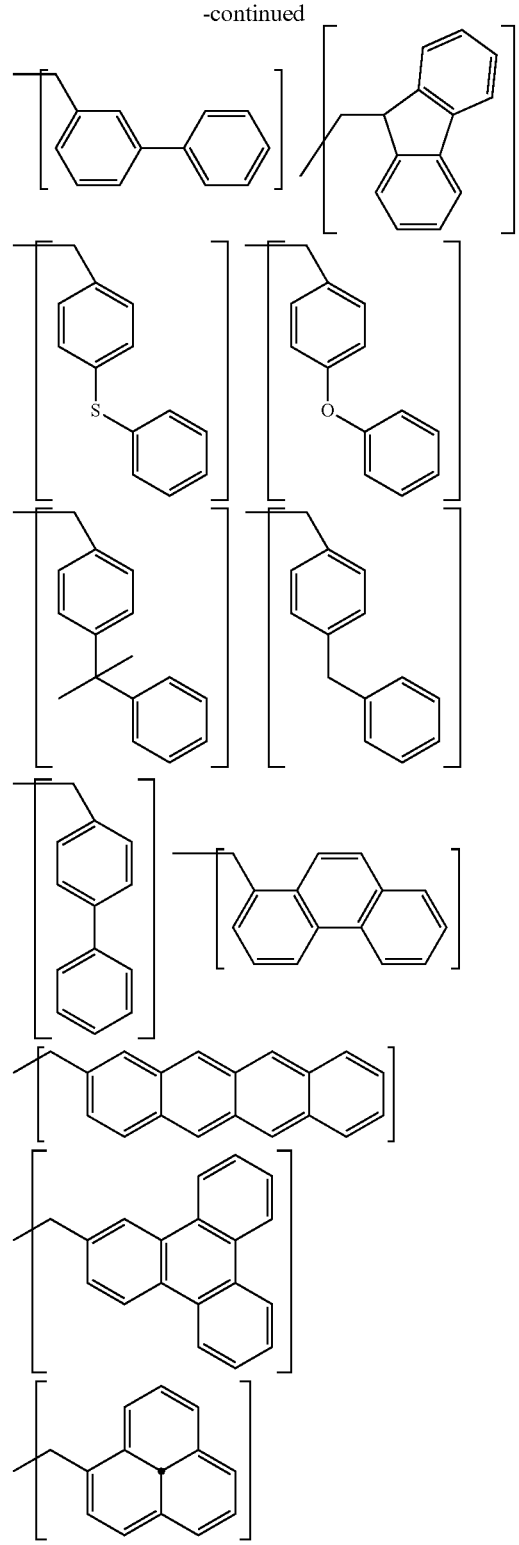

Of these, polycyclic aromatic groups such as anthracenemethyl and pyrenemethyl are most preferred for exposure at 248 nm. A substituent group having an alicyclic or naphthalene structure is preferably used for improved transparency at 193 nm. On the other hand, since the benzene ring has a window for improved transparency at wavelength 157 nm, absorption must be increased by shifting the absorption wavelength. The furan ring has absorption at a shorter wavelength than the benzene ring, and thus exhibits slightly improved absorption at 157 nm, with its effect being faint. The naphthalene, anthracene and pyrene rings exhibit enhanced absorption due to a shift of absorption wavelength to the longer side. Since these aromatic rings have the additional advantage of improved etch resistance, they are preferred for use. The method of introducing the foregoing substituent group is, for example, by introducing an alcohol compound having a hydroxyl group at the site where the substituent group is attached into the naphthalene derivative having formula (1) or (2) or a polymer comprising the same in the presence of an acid catalyst. Suitable acid catalysts are as exemplified above for the novolac forming reaction. Introduction of a substituent group may be conducted concurrently with the novolac forming reaction.

To improve transparency at 193 nm, the naphthalene derivative having formula (1) or (2) or the polymer comprising the same may be hydrogenated. A degree of hydrogenation is preferably up to 80 mol %, more preferably up to 60 mol % based on the aromatic group.

The naphthalene derivative having formula (1) or (2) or the polymer comprising the same (generally referred to as "inventive compound," hereinafter) may be used as a resist bottom layer material in the method for forming a resist bottom layer in the trilayer process. These inventive compounds have very high heat resistance because of inclusion of quaternary carbon and a carbon density which is as high as approximately 90%. When a hard mask in the form of a silicon oxide, silicon nitride or silicon oxynitride film is formed on the resist bottom layer by CVD or similar deposition technique, a high temperature, specifically a temperature above 300° C. in the case of nitride film is necessary, and the resist bottom layer is thus required to have high heat resistance. Since the inventive compounds are benzene ring fused hydrocarbons, they exhibit relatively low absorption at wavelength 193 nm due to an absorption shift, and are expected to exert better antireflective effect at a film thickness of at least 100 nm when used in the trilayer process. Also, the inventive compounds have higher resistance against $CF_4/CHF_3$ gas and $Cl_2/BCl_3$ gas etching used in substrate processing than ordinary m-cresol novolac resins. Since the count of hydrogen atoms becomes smaller by an increment of the aromatic count, etch resistance is improved, and the occurrence of pattern twist during substrate etching is suppressed. By baking at a temperature in excess of 300° C., the bottom layer is endowed with more etch resistance and solvent resistance and the occurrence of pattern twist during substrate etching is suppressed.

The resist bottom layer material used in the method for forming a resist bottom layer in the trilayer process is defined as comprising (A) the naphthalene derivative having formula (1) or (2) or the polymer comprising the same as an essential component and preferably (B) an organic solvent. If it is desired to improve spin coating properties and substrate step burying property as well as the rigidity and solvent resistance of the film, the material may further comprise (C) a blending compound or polymer, (D) a crosslinker, and (E) an acid generator.

The organic solvent (B) used in the bottom layer material may be any desired one as long as components (A) to (E) and other components are dissolvable therein. Suitable solvents which can be added are described in JP-A 2007-199653, paragraphs [0091] and [0092]. Illustrative, non-limiting, examples of the organic solvent include ketones such as cyclohexanone and methyl-2-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate.

These solvents may be used alone or in combinations of two or more thereof.

The organic solvent is preferably added in an amount of 200 to 10,000 parts by weight, especially 300 to 5,000 parts by weight per 100 parts by weight of component (A).

In a preferred embodiment, the resist bottom layer material comprises organic solvent (B), and in a more preferred embodiment, it further comprises crosslinker (D) and acid generator (E) if it is desired to improve spin coating properties and substrate step burying property as well as the rigidity and solvent resistance of the film.

Optionally, another polymer or compound may be blended. When the blending compound or polymer is blended with the naphthalene derivative having formula (1) or (2) or the polymer comprising the same, it can serve the functions of improving film formation by spin coating and burying in stepped substrates. More preferably a choice may be made of materials having a high carbon density and etching resistance. Suitable blending polymers include novolac resins derived from phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-t-butylphenol, 3-t-butylphenol, 4-t-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-t-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-t-butyl-5-methylphenol, pyrogallol, thymol, isothymol, 4,4'-(9H-fluoren-9-ylidene)bisphenol, 2,2'-dimethyl-4,4'-(9H-fluoren-9-ylidene)bisphenol, 2,2'-diallyl-4,4'-(9H-fluoren-9-ylidene)bisphenol, 2,2'-difluoro-4,4'-(9H-fluoren-9-ylidene)bisphenol, 2,2'-diphenyl-4,4'-(9H-fluoren-9-ylidene)bisphenol, 2,2'-dimethoxy-4,4'-(9H-fluoren-9-ylidene)bisphenol, 2,3,2',3'-tetrahydro-(1,1')-spirobiindene-6,6'-diol, 3,3,3',3'-tetramethyl-2,3,2',3'-tetrahydro-(1,1')-spirobiindene-6,6'-diol, 3,3,3',3',4,4'-hexamethyl-2,3,2',3'-tetrahydro-(1,1')-spirobiindene-6,6'-diol, 2,3,2',3'-tetrahydro-(1,1')-spirobiindene-5,5'-diol, 5,5'-dimethyl-3,3,3',3'-tetramethyl-2,3,2',3'-tetrahydro-(1,1')-spirobiindene-6,6'-diol, 1-naphthol, 2-naphthol, 2-methyl-1-naphthol, 4-methoxy-1-naphthol, 7-methoxy-2-naphthol, and dihydroxynaphthalenes such as 1,5-dihydroxynaphthalene, 1,7-dihydroxynaphthalene and 2,6-dihydroxynaphthalene, methyl 3-hydroxy-naphthalene-2-carboxylate, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborn-2-ene, α-pinene, β-pinene, limonene, etc.; and polyhydroxystyrene, polystyrene, polyvinyl naphthalene, polyvinyl anthracene, polyvinyl carbazole, polyindene, polyacenaphthylene, polynorbornene, polycyclodecene, polytetracyclododecene, polynortricyclene, poly(meth)acrylate, and copolymers thereof. Also included are nortricyclene as described in JP-A 2004-205658, hydrogenated naphthol novolac resins as described in JP-A 2004-205676, naphthol dicyclopentadiene copolymers as described in JP-A 2004-205685, phenol dicyclopentadiene copolymers as described in JP-A 2004-354554 and JP-A 2005-010431, fluorene bisphenol novolac resins as described in JP-A 2005-128509, acenaphthylene copolymers as described in JP-A 2005-250434, indene copolymers as described in JP-A 2006-53543, phenol-containing fullerene as described in JP-A 2006-227391, bisphenol compounds and novolac resins thereof as described in JP-A 2006-259249, JP-A 2006-293298, and JP-A 2007-316282, dibisphenol compounds and novolac resins thereof as described in JP-A 2006-259482, novolac resins of adamantane phenol compounds as described in JP-A 2006-285095, hydroxyvinyl naphthalene copolymers as described in JP-A 2007-171895, bisnaphthol compounds and novolac resins thereof as described in JP-A 2007-199653, ROMP polymers as described in JP-A 2008-026600, tricyclopentadiene copolymers and analogous resins as described in JP-A 2008-096684, and fullerene resins as described in JP-A 2006-227391 and JP-A 2008-158002.

The amount of the blending compound or polymer compounded is usually 0 to 1,000 parts by weight, preferably 0 to 500 parts by weight per 100 parts by weight of the naphthalene derivative having formula (1) or (2) or the polymer comprising the same.

One of the functions required for the resist bottom layer additionally having an antireflective function is the elimination of intermixing with the overlying films (i.e., silicon-containing resist middle layer and resist top layer) and the elimination of diffusion of low molecular weight components into the overlying films (see Proc. SPIE Vol. 2195, p 225-229 (1994)). One common means for preventing intermixing and diffusion is by baking an antireflective film as spin coated for inducing thermal crosslinkage. Then, in the event the antireflective film material contains a crosslinker, a method of introducing crosslinkable substituent groups into the polymer may be employed. Even when a particular crosslinker is not added, the naphthalene derivative having formula (1) or (2) or the polymer comprising the same undergoes crosslinkage through the reaction mechanism (to be described later) by heating at a temperature in excess of 350° C.

Since the naphthalene derivative having formula (1) or (2) or the polymer comprising the same has very high heat resistance, it undergoes substantially no pyrolysis even when baked at a high temperature in excess of 350° C. Since baking at a temperature in excess of 350° C. promotes evaporation of the solvent, the film of the inventive compound tends to increase its carbon density and denseness, exhibiting more etch resistance. In addition, baking at a temperature in excess of 350° C. endows the film with more solvent resistance and prevents the film from being twisted during substrate etching. When a less heat resistant material film is baked at a high temperature in excess of 350° C., the film does not always increase its carbon density, because of possible pyrolysis, and may be degraded in some cases. Although baking at a temperature below 350° C. may fail to induce sufficient crosslinkage, the addition of a crosslinker and acid generator ensures to achieve a high carbon density and high denseness by baking at a temperature of at least 150° C., preferably 200° C. to 350° C.

Suitable crosslinkers which can be used herein are described in JP-A 2007-199653, paragraphs [0055] to [0060]. Examples of the crosslinker include melamine compounds, guanamine compounds, glycoluril compounds and urea compounds having substituted thereon at least one group selected from among methylol, alkoxymethyl and acyloxymethyl groups, epoxy compounds, thioepoxy compounds, isocyanate compounds, azide compounds, and compounds having a double bond such as an alkenyl ether group. These compounds may be either used as an additive or introduced into a polymer side chain as a pendant group. Hydroxyl-containing compounds are also useful as the crosslinker. The crosslinker is preferably compounded in an amount of 0 to 50 parts by weight, more preferably 3 to 50 parts by weight per 100 parts by weight of component (A).

An acid generator may be added to the resist bottom layer material to further accelerate the thermally induced crosslinking reaction. Acid generators include those which generate an acid through pyrolysis and those which generate an acid upon exposure to light, and both are useful. The acid generators used herein include those described in JP-A 2007-199653, paragraphs [0061] to [0085]. Suitable acid generators include onium salts, diazomethane derivatives, glyoxime derivatives, bissulfone derivatives, N-hydroxyimide sulfonic acid esters, β-ketosulfonic acid derivatives, disulfone derivatives, nitrobenzyl sulfonate derivatives, and sulfonic acid ester derivatives. The acid generator is preferably compounded in an amount of 0 to 50 parts by weight, more preferably 0.1 to 50 parts by weight per 100 parts by weight of component (A).

In, the resist bottom layer material, a basic compound may be compounded for improving the storage stability. The basic compound plays the role of an acid quencher for preventing a minute amount of an acid generated by the acid generator from facilitating crosslinking reaction. The basic compound which can be added herein may be any of the compounds described in JP-A 2007-199653, paragraphs [0086] to [0090]. Suitable basic compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, and imide derivatives. The basic compound is preferably compounded in an amount of 0 to 2 parts by weight, more preferably 0.001 to 2 parts by weight per 100 parts by weight of component (A).

A surfactant may be added to the resist bottom layer material for improving the applicability by spin coating. Suitable surfactants are described in JP-A 2008-111103, paragraphs [0165] to [0166] (U.S. Pat. No. 7,537,880).

Process

It is now described how to form a pattern using the resist bottom layer material of the invention.

Like photoresists, the resist bottom layer material of the invention can be applied onto a processable substrate by any desired technique such as spin coating, to form a bottom layer thereon. Spin coating and other coating techniques are effective for burying steps. After spin coating, the coating is desirably baked in order to evaporate off the solvent and to promote crosslinking reaction for preventing the bottom layer from intermixing with the resist middle layer and top layer to be subsequently applied thereon. The bake is preferably effected at a temperature of more than 150° C. to 600° C., more preferably 200° C. to 400° C. for a time of 10 to 600 seconds, more preferably 10 to 300 seconds. With thermal impacts such as device damages and wafer deformation taken into account, the upper limit of permissible heating temperature in the lithographic wafer process is up to 600° C., preferably up to 500° C.

As understood from SPIE Vol. 469, p 72 (1984), cited above, when the naphthalene derivative having formula (1) or the polymer comprising the same used in the method for forming a resist bottom layer according to the invention is heated, radicals are created, helping crosslinking reaction take place. Particularly when the polymer comprising the naphthalene derivative having formula (1) contains a methylene or methine group at the benzyl site, benzyl radicals bond with each other, facilitating crosslinking reaction. Since this reaction is a radical reaction in which no molecules are eliminated, the material film does not undergo shrinkage due to crosslinking as long as the material is fully heat resistant.

Although the bake atmosphere may be air, it is sometimes preferred for preventing the resist bottom layer from oxidation to introduce an inert gas such as $N_2$, Ar or He into the atmosphere for reducing the oxygen content. Where it is necessary to control the oxygen concentration for preventing oxidation, the oxygen concentration is preferably up to 1,000 ppm, more preferably up to 100 ppm. It is preferred to prevent the resist bottom layer from oxidation during bake because oxidation can cause an increase of absorption or a drop of etch resistance. On the other hand, bake in air or oxygen-rich gas is sometimes preferable when molecular crosslinking by oxidative coupling is intended.

The thickness of the resist bottom layer may be suitably determined although it is preferably in the range of 30 to 20,000 nm, especially 50 to 15,000 nm. After the resist bottom layer is formed, a silicon-containing resist middle layer and a silicon-free resist top layer are formed thereon in the case of the trilayer process.

According to the process of the invention, a pattern is formed by coating a substrate with the resist bottom layer material comprising the naphthalene derivative having formula (1) or (2) or the polymer comprising the same to form a resist bottom layer thereon, forming a resist top layer of a photoresist composition on the resist bottom layer via an intervening resist middle layer, exposing a predetermined region of the resist top layer to radiation or the like, developing the resist top layer with a developer to form a resist pattern, etching the resist middle layer using the resist pattern as mask, and etching the resist bottom layer and the substrate using the resulting resist middle layer pattern as mask.

In the embodiment wherein the inorganic hard mask middle layer is formed on the resist bottom layer, a silicon oxide film, silicon nitride film or silicon oxynitride (SiON) film is formed by chemical vapor deposition (CVD) or atomic layer deposition (ALD). The formation of nitride film is described in JP-A 2002-334869 and WO 2004/066377. The inorganic hard mask typically has a thickness of 5 to 200 nm, preferably 10 to 100 nm. The most preferred inorganic hard mask is a SiON film which is fully effective as an ARC. Since the substrate reaches a temperature of 300 to 500° C. during deposition of a SiON film, the bottom layer must withstand a temperature of 300 to 500° C. Since the resist bottom layer material comprising the naphthalene derivative having formula (1) or the polymer comprising the same has heat resistance sufficient to withstand a temperature of 300 to 500° C., it is possible to combine a resist bottom layer formed by spin coating with an inorganic hard mask formed by CVD or ALD.

In one embodiment, a photoresist film is formed on the resist middle layer as the resist top layer. In another embodiment, an organic antireflective coating film (BARC) is formed on the resist middle layer by spin coating, and a photoresist film formed thereon. Where the resist middle layer is a SiON film, an antireflective film consisting of two layers, SiON and BARC films functions to suppress reflection even in the immersion lithography with a high NA in excess of 1.0. Another advantage arising from formation of BARC is to reduce footing of the photoresist pattern immediately above SiON. The BARC film is preferably made of ordinary BARC materials used in the ArF lithography, for example, ARC-29A and ARC-93 by Nissan Chemical Industries, Ltd. and AR-40 by Rohm & Haas. The BARC film preferably has a thickness of 300 to 1,000 Å.

Also preferred as the silicon-containing resist middle layer in the trilayer process is a middle layer based on polysilsesquioxane. Reflection may be suppressed by endowing the resist middle layer with the ARC function. Suitable silsesquioxane-based silicon compounds are described, for example, in JP-A 2004-310019, 2005-015779, 2005-018054, 2005-352104, 2007-065161, 2007-163846, 2007-226170, and 2007-226204. Particularly for 193 nm exposure, when an aromatic rich material having high resistance to substrate etching is used as the resist bottom layer, that resist bottom layer has a high value of k and allows high substrate reflection. However, if reflection can be suppressed by the resist middle layer, then totally the substrate reflection can be suppressed to or below 0.5%. Preferred as the resist middle layer capable of suppressing reflection is anthracene for the 248 nm and 157 nm exposures, or polysilsesquioxane having a pendant in the form of a phenyl or photo-absorptive group having a silicon-silicon bond and capable of acid or heat-induced crosslinking for the 193 nm exposure. The resist middle layer preferably has a thickness of 20 to 100 nm.

For forming the silicon-containing resist middle layer, spin coating is simple and cost effective as compared with CVD.

The resist top layer in the trilayer resist film may be either positive or negative and may be any of commonly used photoresist compositions. When the photoresist composition is applied to form a single-layer resist top layer, a spin coating technique is preferably used as in the case of the resist bottom layer. The photoresist composition is spin coated and then pre-baked, preferably at 60 to 180° C. for 10 to 300 seconds. Thereafter, the resist layer is routinely exposed to radiation through a desired pattern, post-exposure baked (PEB) and developed with a developer, obtaining a resist pattern. The thickness of the resist top layer is preferably in a range of 30 to 500 nm, more preferably 50 to 400 nm, though not particularly limited. The radiation for exposure may be selected from among high-energy radiation having a wavelength of up to 300 nm, specifically excimer laser beams of 248 nm, 193 nm and 157 nm, soft X-ray (EUV) of 3 to 20 nm, electron beam (EB), and X-ray.

Next, etching is carried out using the resist pattern as mask. In the trilayer process, the resist middle layer, specifically inorganic hard mask is etched with fluorocarbon-base gas using the resist pattern as mask. Then the resist bottom layer is etched with oxygen or hydrogen gas using the resist middle layer pattern, specifically inorganic hard mask pattern as mask.

Next, the processable substrate is etched by a standard technique. For example, when the substrate is $SiO_2$, SiN or silica-base low-dielectric-constant insulating film, etching with a fluorocarbon-base gas is employed. When the substrate is p-Si, Al or W, etching with a chlorine or bromine-base gas is employed. When the substrate processing is etching with a fluorocarbon-base gas, the silicon-containing middle layer in the trilayer process is stripped at the same time as the substrate processing. When the substrate is etched with a chlorine or bromine-base gas, the silicon-containing middle layer must be subsequently stripped by dry etching with a fluorocarbon-base gas after the substrate processing.

The resist bottom layer formed by the inventive method is characterized by resistance to etching of the processable substrate. The processable substrate may be a substrate having a processable layer deposited thereon. The substrate includes those of Si, α-Si, p-Si, $SiO_2$, SiN, SiON, W, TiN, Al and the like, and a suitable material different from the processable layer is selected among them. The processable layer is selected from low-k films of Si, SiO$_2$, SiON, SiN, p-Si, α-Si, W, W—Si, Al, Cu, Al—Si, and the like and stop films thereof, and typically has a thickness of 50 to 10,000 nm, especially 100 to 5,000 nm.

Figure 1B:
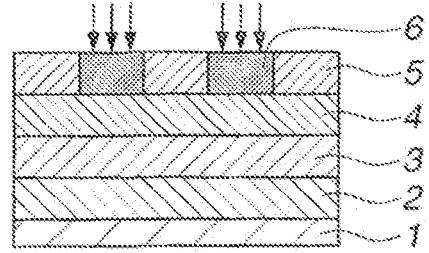
Figure 1C:
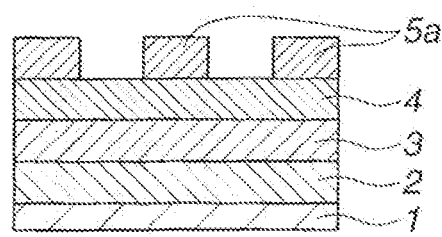
Figure 1D:
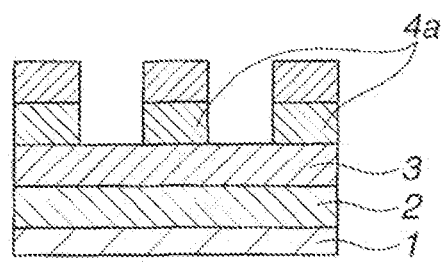
Figure 1E:
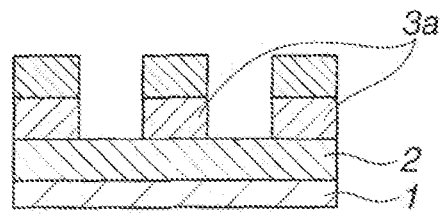
Figure 1F:
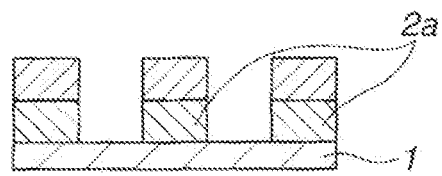
Figure 3:
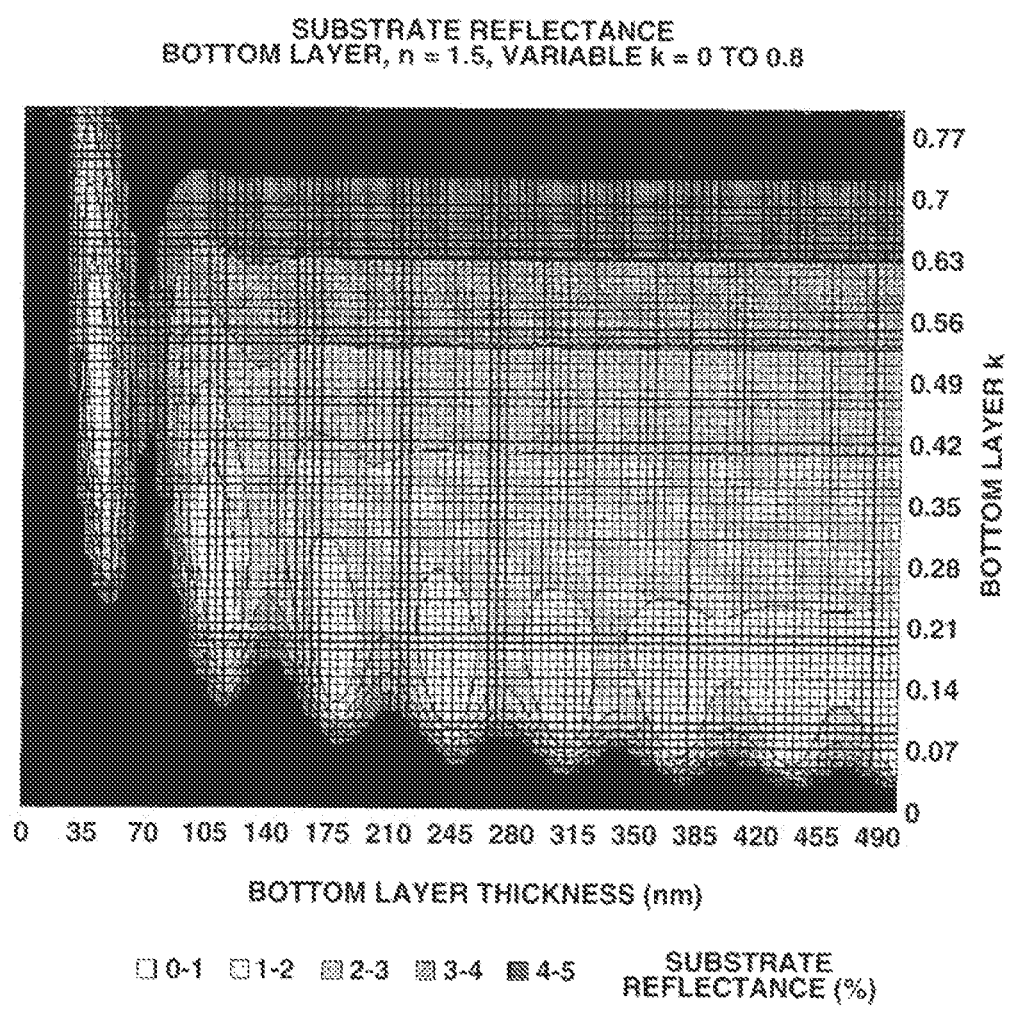
FIG. 3 is a graph plotting the substrate reflectance versus bottom layer thickness in bilayer process when the n value of the bottom layer is fixed at 1.5 and the k value varies from 0 to 0.8.
Figure 4:
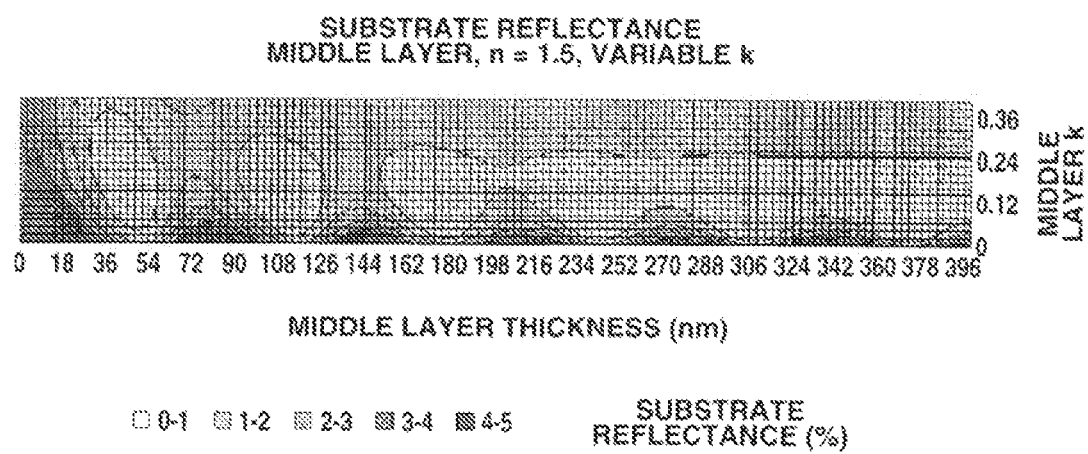
FIG. 4 is a graph plotting the substrate reflectance in trilayer process when the bottom layer has a fixed n of 1.5, a fixed k of 0.6 and a fixed thickness of 500 nm, and the middle layer has a fixed n of 1.5, a k value varying from 0 to 0.3 and a thickness varying from 0 to 400 nm.
Figure 5:
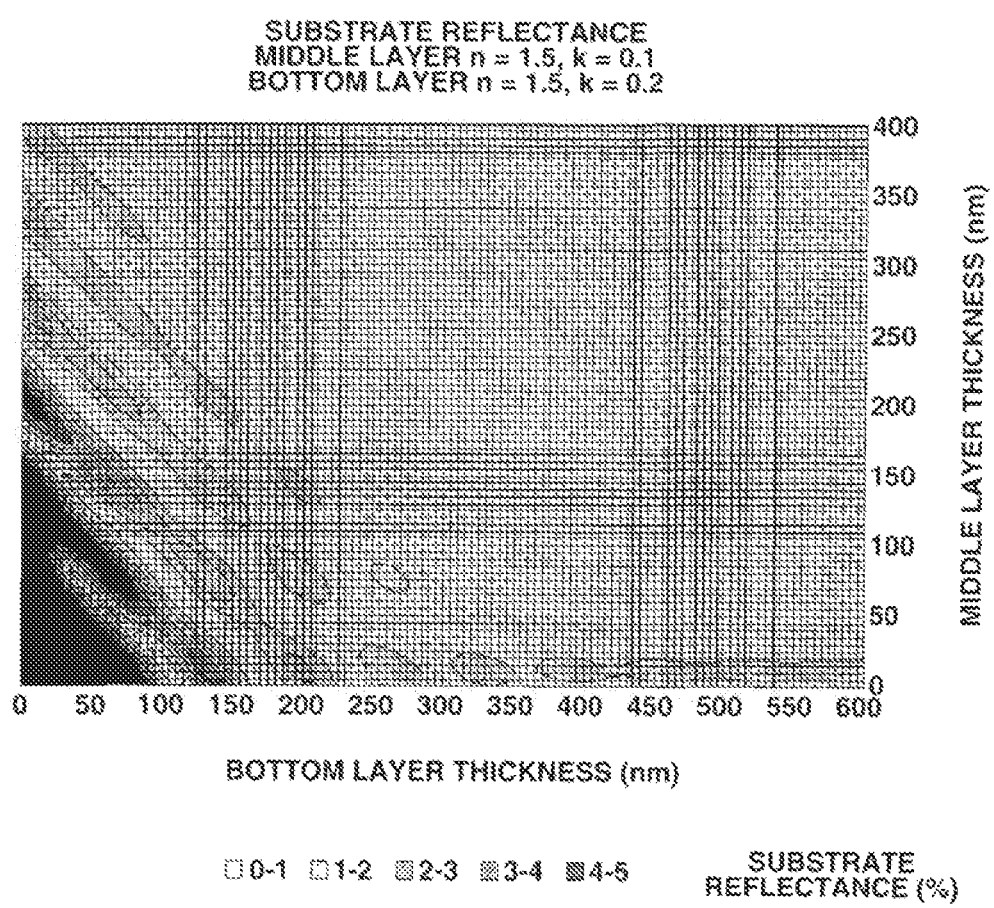
FIG. 5 is a graph plotting the substrate reflectance versus varying thickness of the bottom layer and middle layer in trilayer process when the bottom layer has a fixed n of 1.5 and a fixed k of 0.2, and the middle layer has a fixed n of 1.5 and a fixed k of 0.1.

Referring to FIG. 1, the trilayer resist working process is described. A resist bottom layer 3 is formed on a processable layer 2 lying on a substrate 1, a resist middle layer 4 is formed on the bottom layer 3, and a resist top layer 5 is formed thereon (FIG. 1A). Then a predetermined region 6 of the resist top layer is exposed to radiation (FIG. 1B), PEB, and developed, forming a resist pattern 5a (FIG. 1C). The resist middle layer 4 is etched with CF gas through the resist pattern 5a as mask, forming a resist middle layer pattern 4a (FIG. 1D). The resist pattern 5a is removed, and the resist bottom layer 3 is etched with oxygen plasma through the resist middle layer pattern 4a as mask, forming a resist bottom layer pattern 3a (FIG. 1E). The resist middle layer pattern 4a is removed, and the processable layer 2 is etched through the resist bottom layer pattern 3a as mask, forming a pattern 2a on the substrate 1 (FIG. 1F).

In the embodiment using an inorganic hard mask middle layer, the resist middle layer 4 is the inorganic hard mask middle layer. In the other embodiment using BARC, a BARC layer intervenes between the resist middle layer 4 and the resist top layer 5. Etching of BARC may be continuously followed by etching of the resist middle layer 4. Alternatively, etching of BARC alone is performed, and after the etching system is exchanged, etching of the resist middle layer 4 is performed.

EXAMPLE

Synthesis Examples and Examples are given below together with Comparative Examples for further illustrating the invention although the invention is not limited thereby.

The weight average molecular weight (Mw) and number average molecular weight (Mn) of a polymer are determined by gel permeation chromatography (GPC) versus polystyrene standards, and a dispersity (Mw/Mn) is computed therefrom.

Synthesis Example 1

Synthesis of Naphthalene Derivative (6)

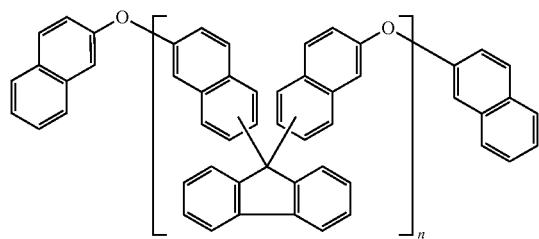

(6)

(1-1)

A three-neck flask was charged with 30.0 g (111 mmol) of 2,2'-dinaphthyl ether, 20.0 g (111 mmol) of 9-fluorenone, and 120 ml of 1,2-dichloroethane, which were dissolved by keeping the flask in an oil bath. After dissolution was confirmed, 0.6 ml of 3-mercaptopropionic acid and 6.0 ml of methanesulfonic acid were added dropwise. Under reflux, reaction was effected for 13 hours. At the end of reaction, the reaction solution was diluted with 500 ml of toluene, and transferred to a separatory funnel where it was washed with water and separated. Water washing was repeated until the water layer became neutral. The organic layer was concentrated under reduced pressure, and 250 ml of tetrahydrofuran (THF) was added to the residue, which was poured to 2,250 ml of hexane, allowing the polymer to crystallize. The crystallized polymer was collected by filtration and dried in vacuum, obtaining naphthalene derivative (6).

Naphthalene Derivative (6):
Mw=2,867
Mw/Mn=1.95
IR (KBr) νmax=3055, 1910, 1596, 1502, 1463, 1255, 1219, 1193, 1165 cm$^{-1}$
n=~6.0 (computed from Mw), ~5.45 (computed from $^{13}$C-NMR)
TG-DTA (air, 30→500° C.): −9.37%
TG-DTA (He, 30→500° C.): −11.87%

These TG-DTA data demonstrate that the compound has high heat resistance and prove a progress of crosslinking reaction due to oxidative coupling in air.

(1-2)

A three-neck flask was charged with 7.50 g (27.7 mmol) of 2,2'-dinaphthyl ether, 5.0 g (27.7 mmol) of 9-fluorenone, and 30 ml of 1,2-dichloroethane, which were dissolved by keeping the flask in an oil bath. After dissolution was confirmed, 0.15 ml of 3-mercaptopropionic acid and 1.5 ml of methanesulfonic acid were added dropwise. Under reflux, reaction was effected for 8 hours. At the end of reaction, the reaction solution was quenched with 50 ml of saturated sodium hydrogen carbonate aqueous solution, diluted with 120 ml of THF and 30 ml of toluene, and transferred to a separatory funnel where separation was carried out. The organic layer was washed with water and saturated saline, and dried over sodium sulfate. After the sodium sulfate was filtered off, the filtrate was concentrated under reduced pressure, and 50 ml of THF was added to the residue, which was poured to 500 ml of hexane, allowing the polymer to crystallize. The crystallized polymer was collected by filtration and dried in vacuum, obtaining naphthalene derivative (6).

Naphthalene Derivative (6):
Mw=2,388
Mw/Mn=1.69
n=~4.90 (computed from Mw), ~5.01 (computed from $^{13}$C-NMR)

(1-3)

A three-neck flask was charged with 7.5 g (27.7 mmol) of 2,2'-dinaphthyl ether, 5.0 g (27.7 mmol) of 9-fluorenone, and 30 ml of 1,2-dichloroethane, which were dissolved by keeping the flask in an oil bath. After dissolution was confirmed, 0.15 ml of 3-mercaptopropionic acid and 1.5 ml of methanesulfonic acid were added dropwise. Under reflux, reaction was effected for 6.5 hours. At the end of reaction, the reaction solution was quenched with 50 ml of saturated sodium hydrogen carbonate aqueous solution, diluted with 120 ml of THF and 30 ml of toluene, and transferred to a separatory funnel where separation was carried out. The organic layer was washed with water and saturated saline, and dried over sodium sulfate. After the sodium sulfate was filtered off, the filtrate was concentrated under reduced pressure, and 50 ml of THF was added to the residue, which was poured to 500 ml of hexane, allowing the polymer to crystallize. The crystallized polymer was collected by filtration and dried in vacuum, obtaining naphthalene derivative (6).

Naphthalene Derivative (6):
Mw=1,738
Mw/Mn=1.52
n=~4.39 (computed from Mw), ~3.77 (computed from $^{13}$C-NMR)

Synthesis Example 2

Synthesis of Naphthalene Derivative (7)

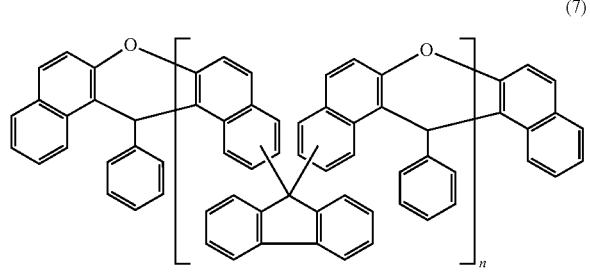

(7)

A three-neck flask was charged with 9.94 g (27.7 mmol) of 14-(2-naphthyl)-14H-dibenzo[a,j]xanthene, 5.0 g (27.7 mmol) of 9-fluorenone, and 30 ml of 1,2-dichloroethane, which were dissolved by keeping the flask in an oil bath. After dissolution was confirmed, 0.6 ml of 3-mercaptopropionic acid and 6.0 ml of methanesulfonic acid were added dropwise. Under reflux, reaction was effected for 23 hours. At the end of reaction, the reaction solution was quenched with 50 ml of saturated sodium hydrogen carbonate aqueous solution, diluted with 120 ml of THF and 30 ml of toluene, and transferred to a separatory funnel where separation was carried out. The organic layer was washed with water and saturated saline, and dried over sodium sulfate. After the sodium sulfate was filtered off, the filtrate was concentrated under reduced pressure, and 70 ml of THF was added to the residue, which was poured to 600 ml of methanol, allowing the polymer to crystallize. The crystallized polymer was collected by filtration and dried in vacuum, obtaining naphthalene derivative (7).

Naphthalene Derivative (7):
Mw=2,651
Mw/Mn=1.80
n=~4.4 (computed from Mw), ~3.82 (computed from $^{13}$C-NMR)
IR (D-ATR) vmax=3060, 1749, 1593, 1460, 1401, 1243 cm$^{-1}$
TG-DTA (air, 30→500° C.) −16.44%
TG-DTA (He, 30→500° C.): −8.09%
A weight loss due to oxidation was observed when heated in air above 400° C.

Synthesis Example 3

Synthesis of Naphthalene Derivative (8)

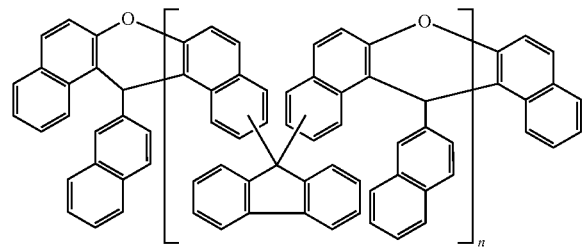

(8)

A three-neck flask was charged with 11.3 g (27.7 mmol) of 14-phenyl-14H-dibenzo[a,j]xanthene, 5.0 g (27.7 mmol) of 9-fluorenone, and 30 ml of 1,2-dichloroethane, which were dissolved by keeping the flask in an oil bath. After dissolution was confirmed, 0.15 ml of 3-mercaptopropionic acid and 1.5 ml of methanesulfonic acid were added dropwise. Under reflux, reaction was effected for 18 hours. At the end of reaction, the reaction solution was diluted with 250 ml of THF and 80 ml of toluene, and transferred to a separatory funnel where it was washed with water and separated. Water washing was repeated until the water layer became neutral. The organic layer was concentrated under reduced pressure, and 70 ml of THF was added to the residue, which was poured to 800 ml of diisopropyl ether, allowing the polymer to crystallize. The crystallized polymer was collected by filtration and dried in vacuum, obtaining naphthalene derivative (8).

Naphthalene Derivative (8):
Mw=4,102
Mw/Mn=2.08
IR (KBr) vmax=3057, 1907, 1749, 1593, 1461, 1400, 1243 cm$^{-1}$
n=~9.91 (computed from Mw), ~6.73 (computed from $^{13}$C-NMR)
TG-DTA (air, 30→500° C.): −22.05%
TG-DTA (He, 30→500° C.): −7.56%
A weight loss due to oxidation was observed when heated in air above 350° C.

Synthesis Example 4

Synthesis of Naphthalene Derivative (9)

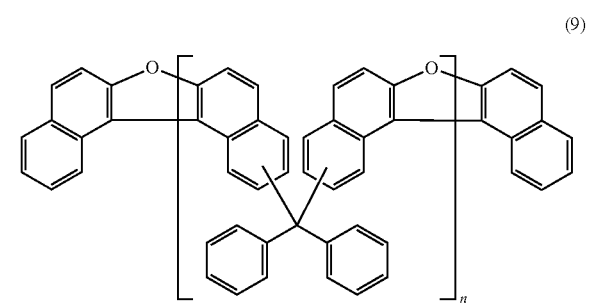

(9)

(4-1)

A three-neck flask was charged with 7.44 g (27.7 mmol) of dinaphtho[2,1-b:1',2'-d]furan, 5.0 g (27.7 mmol) of 9-fluorenone, and 100 ml of 1,2-dichloroethane, which were dissolved by keeping the flask in an oil bath. After dissolution was confirmed, 0.15 ml of 3-mercaptopropionic acid and 1.5 ml of methanesulfonic acid were added dropwise. Under reflux, reaction was effected for 30 hours. At the end of reaction, the reaction solution was quenched with 50 ml of saturated sodium hydrogen carbonate aqueous solution, diluted with 200 ml of THF and 60 ml of toluene, and transferred to a separatory funnel where separation was carried out. The organic layer was washed with water and saturated saline, and dried over sodium sulfate. After the sodium sulfate was filtered off, the filtrate was concentrated under reduced pressure, and 50 ml of THF was added to the residue, which was poured to 500 ml of methanol, allowing the polymer to crystallize. The crystallized polymer was collected by filtration and dried in vacuum, obtaining naphthalene derivative (9).

Naphthalene Derivative (9):
Mw=3,050
Mw/Mn=1.69
IR (D-ATR) vmax=3055, 1912, 1735, 1582, 1447, 1377, 1238 cm$^{-1}$ n=~7.46 (computed from Mw), ~6.78 (computed from $^{13}$C-NMR)
TG-DTA (air, 30→500° C.): −9.57%
TG-DTA (He, 30→500° C.): −6.44%

A weight loss due to oxidation was observed when heated in air above 350° C.

(4-2)

A three-neck flask was charged with 16.79 g (93.0 mmol) of dinaphtho[2,1-b:1',2'-d]furan, 25.0 g (93.0 mmol) of 9-fluorenone, and 100 ml of 1,2-dichloroethane, which were dissolved by keeping the flask in an oil bath. After dissolution was confirmed, 0.50 ml of 3-mercaptopropionic acid and 5.0 ml of methanesulfonic acid were added dropwise. Under reflux, reaction was effected for 35.5 hours. At the end of reaction, the reaction solution was diluted with 500 ml of THF and 150 ml of toluene, and transferred to a separatory funnel where it was washed with water and separated. Water washing was repeated until the water layer became neutral. The organic layer was concentrated under reduced pressure, and 160 ml of THF was added to the residue, which was poured to 1,700 ml of methanol, allowing the polymer to crystallize. The crystallized polymer was collected by filtration and dried in vacuum, obtaining naphthalene derivative (9).

Naphthalene Derivative (9):
Mw=2,939
Mw/Mn=2.07
n=~7.20 (computed from Mw), ~5.90 (computed from $^{13}$C-NMR)

A three-neck flask was charged with 11.74 g (43.4 mmol) of 2,2'-dinaphthyl ether, 10.0 g (43.4 mmol) of 9-benzo[b]fluorenone, and 60 ml of 1,2-dichloroethane, which were dissolved by keeping the flask in an oil bath. After dissolution was confirmed, 0.30 ml of 3-mercaptopropionic acid and 3.0 ml of methanesulfonic acid were added dropwise. Under reflux, reaction was effected for 35.5 hours. At the end of reaction, the reaction solution was diluted with 250 ml of THF and 300 ml of toluene, and transferred to a separatory funnel where it was washed with water and separated. Water washing was repeated until the water layer became neutral. The organic layer was concentrated under reduced pressure, and 120 ml of THF was added to the residue, which was poured to 1,000 ml of hexane, allowing the polymer to crystallize. The crystallized polymer was collected by filtration and dried in vacuum, obtaining naphthalene derivative (10).

Naphthalene Derivative (10):
Mw=3,774
Mw/Mn=2.12
IR (KBr) vmax=3052, 1911, 1708, 1596, 1502, 1464, 1255, 1219, 1166 cm$^{-1}$
n=~7.3 (computed from Mw), ~7.06 (computed from $^{13}$C-NMR)
TG-DTA (air, 30→500° C.): −6.20%
TG-DTA (He, 30→500° C.): −7.57%

Synthesis Example 6

Synthesis of Naphthalene Derivative (11), i.e., Novolac Resin of Naphthalene Derivative (6) with Formaldehyde

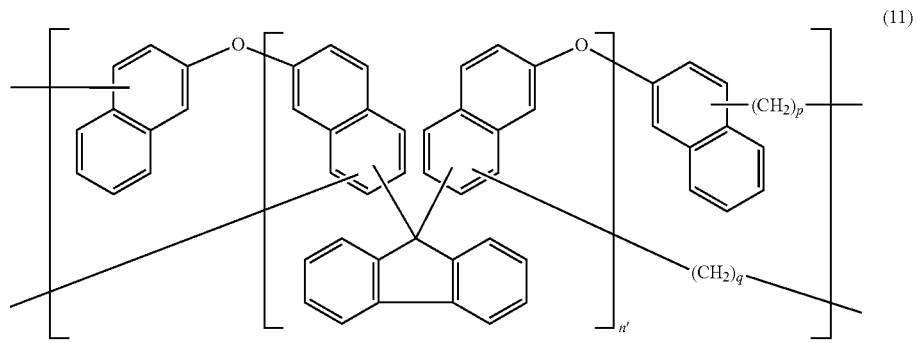

Synthesis Example 5

Synthesis of Naphthalene Derivative (10)

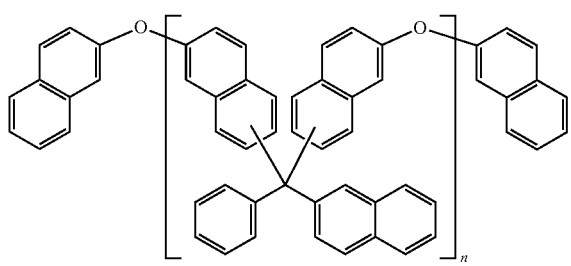

A three-neck flask was charged with 2.0 g of naphthalene derivative (6) (Mw=2,867, n=~6.0 (computed from Mw), ~5.45 (computed from $^{13}$C-NMR)) and 20 ml of 1,2-dichloroethane, which were dissolved by keeping the flask in an oil bath. After dissolution was confirmed, 0.044 g of paraformaldehyde (formaldehyde content 94 wt %) was added to the solution, which was stirred for 5 minutes, and 0.05 ml of trifluoromethanesulfonic acid was added dropwise. Under reflux, reaction was effected for 2 hours. At the end of reaction, 50 ml of THF was added, the insoluble matter was filtered off, and the filtrate was diluted with 20 ml of toluene and transferred to a separatory funnel where it was washed with water and separated. Water washing was repeated until the water layer became neutral. The organic layer was evaporated to dryness, obtaining naphthalene derivative (11).

Naphthalene Derivative (11):
Mw=6,591
Mw/Mn=3.05
IR (KBr) vmax=3055, 2953, 1906, 1716, 1595, 1502, 1463, 1254, 1221, 1160 cm$^{-1}$

Synthesis Example 7

Synthesis of Naphthalene Derivative (12), i.e., Novolac Resin of Naphthalene Derivative (6) with 2-Naphthaldehyde Naphthalene Derivative (12):
Mw=4,121
Mw/Mn=1.82
IR (KBr) νmax=3054, 1906, 1753, 1595, 1503, 1462, 1253, 1219, 1164 cm$^{-1}$

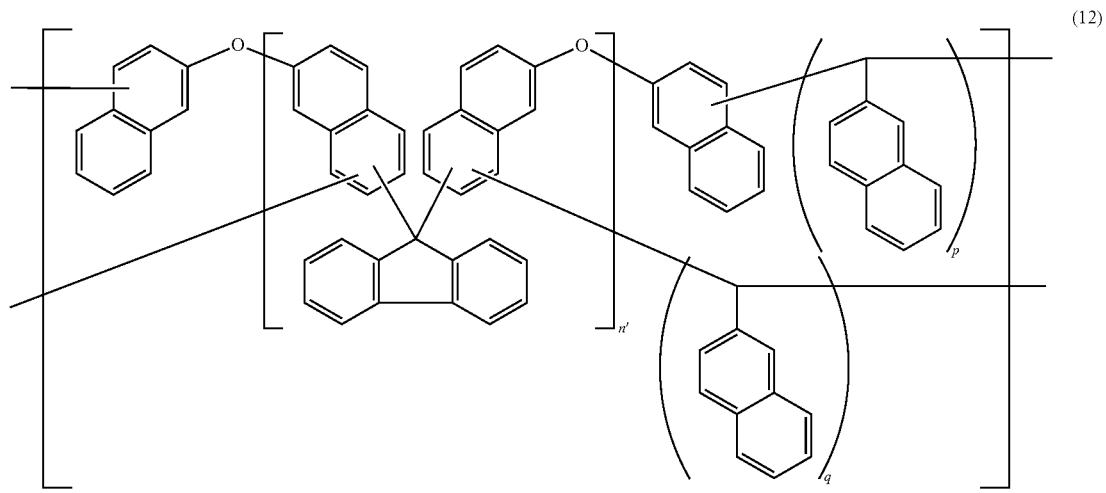

(12)

A three-neck flask was charged with 5.0 g of naphthalene derivative (6) (Mw=2,867, n=~6.0 (computed from Mw), ~5.45 (computed from $^{13}$C-NMR)), 0.22 g (1.39 mmol) of 2-naphthaldehyde, and 20 ml of 1,2-dichloroethane, which were dissolved by keeping the flask in an oil bath. After dissolution was confirmed, 0.05 ml of trifluoromethanesulfonic acid was added dropwise. Under reflux, reaction was effected for 3 hours. At the end of reaction, the reaction solution was diluted with 50 ml of THF and 50 ml of toluene and transferred to a separatory funnel where it was washed with water and separated. Water washing was repeated until the water layer became neutral. The organic layer was concentrated under reduced pressure, 10 ml of THF was added to the residue, which was poured into 100 ml of hexane, allowing the polymer to crystallize. The polymer crystallized was collected by filtration and dried in vacuum, obtaining naphthalene derivative (12).

p+q=~2.84 (computed from $^{13}$C-NMR)
n=~7.22 (computed from $^{13}$C-NMR)

Synthesis Example 8

Synthesis of Naphthalene Derivative (13), i.e., Oxidative Coupling of Naphthalene Derivative (6)

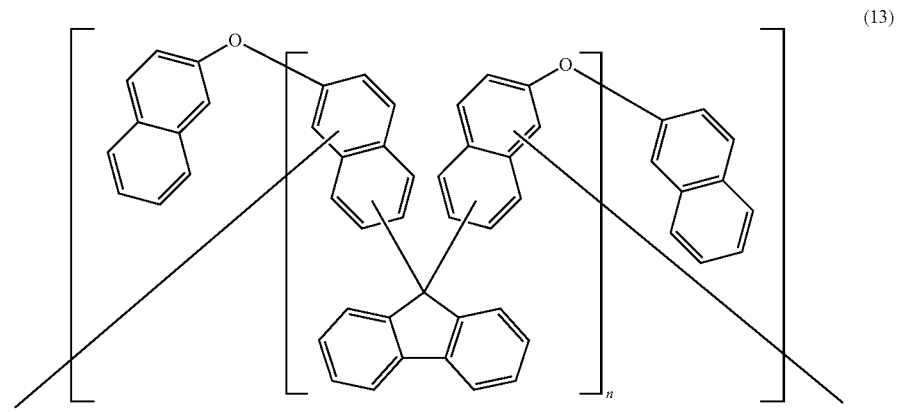

(13)

A flask was charged with 20.0 g of naphthalene derivative (6) (Mw=2,867, n=~6.0 (computed from Mw), ~5.45 (computed from $^{13}$C-NMR)) and 0.27 g (0.58 mmol) of di-μ-hydroxo-bis[(N,N,N',N'-tetramethylethylenediamine)-copper(II)]chloride, which were dissolved in 58 ml of 2-methoxyethanol. In an air open system at room temperature, reaction was carried out for 12 hours. The reaction was quenched with 50 ml of 1N hydrochloric acid aqueous solution. The reaction solution was extracted with 150 ml of methyl ethyl ketone and 25 ml of toluene, washed with water and separated. Water washing/separation was repeated until the water layer became neutral. The organic layer was concentrated under reduced pressure, and 50 ml of THF was added to the residue, which was poured into 100 ml of hexane, allowing the polymer to crystallize. The polymer crystallized was collected by filtration and dried in vacuum, obtaining naphthalene derivative (13).

Naphthalene Derivative (13):
Mw=4,563
Mw/Mn=2.52
IR (KBr) vmax=3052, 1907, 1753, 1595, 1503, 1462, 1253, 1220, 1164 cm$^{-1}$ Polymers 1 to 8 correspond to the naphthol derivatives obtained in Synthesis Examples 1 to 8, respectively, as tabulated in Tables 1-1 and 1-2. Comparative Polymers 9 to 11 are tabulated in Table 1-4. Bottom layer materials were prepared by dissolving a base polymer (selected from Polymers 1 to 8 and Comparative Polymers 9 to 11), Additive 1 or 2, crosslinker XL, and thermal acid generator TAG1, as shown in Table 1-3, in a solvent in accordance with the formulation shown in Table 2 and filtering through a fluoroplastic filter with a pore size of 0.1 The solvent contained a surfactant FC-4430 (3M-Sumitomo Co., Ltd.).

TABLE 1-1

| | | Synthesis Example | Mw | Mw/Mn |
|---|---|---|---|---|
| Polymer 1 | [structure] | Synthesis Example 1-1 Naphthalene derivative (6) | 2,867 | 1.95 |
| Polymer 2 | [structure] | Synthesis Example 4-1 Naphthalene derivative (9) | 3,050 | 1.69 |
| Polymer 3 | [structure] | Synthesis Example 5 Naphthalene derivative (10) | 3,774 | 2.12 |
| Polymer 4 | [structure] | Synthesis Example 2 Naphthalene derivative (7) | 2,651 | 1.80 |

TABLE 1-2

| | | Synthesis Example | Mw | Mw/Mn |
|---|---|---|---|---|
| Polymer 5 | (structure) | Synthesis Example 3 Naphthalene derivative (8) | 4,102 | 2.08 |
| Polymer 6 | (structure) | Synthesis Example 8 Naphthalene derivative (13) | 4,563 | 2.52 |
| Polymer 7 | (structure) | Synthesis Example 6 Naphthalene derivative (11) | 6,591 | 3.05 |
| Polymer 8 | (structure) | Synthesis Example 7 Naphthalene derivative (12) | 4,121 | 1.82 |

TABLE 1-3
| | | |
|---|---|---|
| Additive 1 | 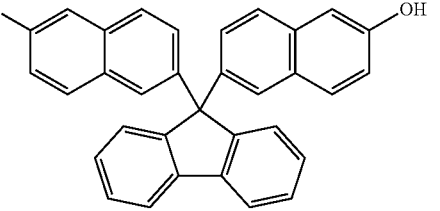 | |
| Additive 2 | 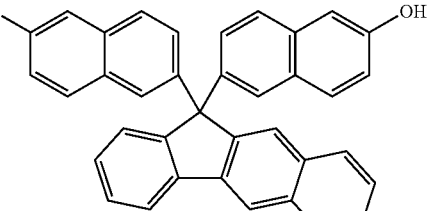 | |
| TAG1 | 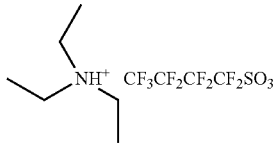 | |
| XL1 | 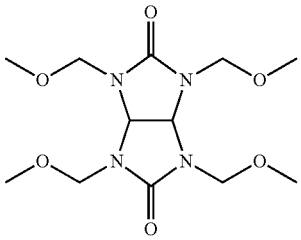 | |
TABLE 1-4
| | | Mw | Mw/Mn |
|---|---|---|---|
| Comparative Polymer 9 | 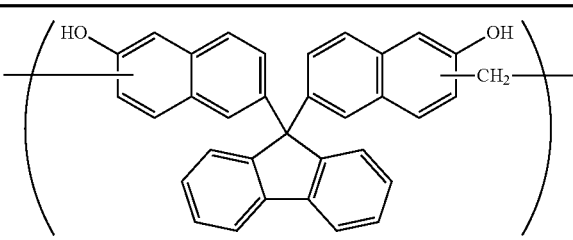 | 4,300 | 4.30 |
| Comparative Polymer 10 | 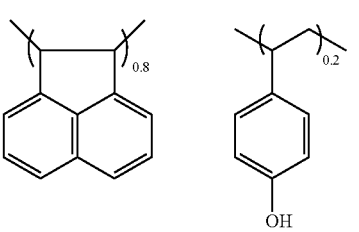 | 7,600 | 1.96 |

TABLE 1-4-continued

|  |  | Mw | Mw/Mn |
|---|---|---|---|
| Comparative Polymer 11 | (structure: fluorene-bisphenol methylene polymer with HO-C6H4- and -C6H4-OH groups attached to 9,9'-position of fluorene, linked by CH2) | 13,000 | 4.33 |

TABLE 2

| Formulation | Base polymer (pbw) | Additive (pbw) | Acid generator (pbw) | Crosslinker (pbw) | Solvent (pbw) | | Bake temp./time | Refractive index at 193 nm | |
|---|---|---|---|---|---|---|---|---|---|
|  |  |  |  |  |  |  |  | n value | k value |
| UDL-1 | Polymer 1 (15) | — | — | — | PGMEA(30) | CyH(70) | 350° C./60 sec. |  |  |
| UDL-2 | Polymer 2 (15) | — | — | — | PGMEA(30) | CyH(70) | 350° C./60 sec. | 130 | 0.44 |
| UDL-3 | Polymer 3 (15) | — | — | — | PGMEA(30) | CyH(70) | 350° C./60 sec. | 130 | 0.44 |
| UDL-4 | Polymer 4 (15) | — | — | — | PGMEA(30) | CyH(70) | 350° C./60 sec. | 130 | 0.44 |
| UDL-5 | Polymer 5 (15) | — | — | — | PGMEA(30) | CyH(70) | 350° C./60 sec. | 130 | 0.44 |
| UDL-6 | Polymer 6 (15) | — | — | — | PGMEA(30) | CyH(70) | 350° C./60 sec. | 130 | 0.44 |
| UDL-7 | Polymer 7 (15) | — | — | — | PGMEA(30) | CyH(70) | 350° C./60 sec. | 130 | 0.44 |
| UDL-8 | Polymer 8 (15) | — | — | — | PGMEA(30) | CyH(70) | 350° C./60 sec. | 130 | 0.44 |
| UDL-9 | Polymer 1 (7.5) | Additive 1 (7.5) | — | — | PGMEA(30) | CyH(70) | 350° C./60 sec. | 130 | 0.44 |
| UDL-10 | Polymer 2 (7.5) | Additive 1 (7.5) | — | — | PGMEA(30) | CyH(70) | 350° C./60 sec. | 130 | 0.44 |
| UDI-11 | Polymer 3 (7.5) | Additive 1 (7.5) | — | — | PGMEA(30) | CyH(70) | 350° C./60 sec. | 130 | 0.44 |
| UDL-12 | Polymer 4 (7.5) | Additive 1 (7.5) | — | — | PGMEA(30) | CyH(70) | 350° C./60 sec. | 130 | 0.44 |
| UDL-13 | Polymer 5 (7.5) | Additive 1 (7.5) | — | — | PGMEA(30) | CyH(70) | 350° C./60 sec. | 130 | 0.44 |
| UDL-14 | Polymer 6 (7.5) | Additive 1 (7.5) | — | — | PGMEA(30) | CyH(70) | 350° C./60 sec. | 130 | 0.44 |
| UDL-15 | Polymer 7 (7.5) | Additive 1 (7.5) | — | — | PGMEA(30) | CyH(70) | 350° C./60 sec. | 130 | 0.44 |
| UDL-16 | Polymer 8 (7.5) | Additive 1 (7.5) | — | — | PGMEA(30) | CyH(70) | 350° C./60 sec. | 130 | 0.44 |
| UDL-17 | Polymer 1 (7.5) | Additive 2 (7.5) | — | — | PGMEA(30) | CyH(70) | 350° C./60 sec. | 130 | 0.44 |
| UDL-18 | Polymer 2 (7.5) | Additive 2 (7.5) | — | — | PGMEA(30) | CyH(70) | 350° C./60 sec. | 130 | 0.44 |
| UDL-19 | Polymer 3 (7.5) | Additive 2 (7.5) | — | — | PGMEA(30) | CyH(70) | 350° C./60 sec. | 130 | 0.44 |
| UDL-20 | Polymer 1 (7.5) | Additive 1 (7.5) | TAG1 (2) | XL1 (10) | PGMEA(30) | CyH(70) | 230° C./60 sec. | 130 | 0.44 |
| UDL-21 | Polymer 2 (7.5) | Additive 1 (7.5) | TAG1 (2) | XL1 (10) | PGMEA(30) | CyH(70) | 230° C./60 sec. | 130 | 0.44 |
| UDL-22 | Polymer 3 (7.5) | Additive 1 (7.5) | TAG1 (2) | XL1 (10) | PGMEA(30) | CyH(70) | 230° C./60 sec. | 130 | 0.44 |
| UDL-23 | Polymer 4 (7.5) | Additive 1 (7.5) | TAG1 (2) | XL1 (10) | PGMEA(30) | CyH(70) | 230° C./60 sec. | 130 | 0.44 |
| UDL-24 | Polymer 5 (7.5) | Additive 1 (7.5) | TAG1 (2) | XL1 (10) | PGMEA(30) | CyH(70) | 230° C./60 sec. | 130 | 0.44 |
| UDL-25 | Polymer 6 (7.5) | Additive 1 (7.5) | TAG1 (2) | XL1 (10) | PGMEA(30) | CyH(70) | 230° C./60 sec. | 130 | 0.44 |
| UDL-26 | Polymer 7 (7.5) | Additive 1 (7.5) | TAG1 (2) | XL1 (10) | PGMEA(30) | CyH(70) | 230° C./60 sec. | 130 | 0.44 |
| UDL-27 | Polymer 8 (7.5) | Additive 1 (7.5) | TAG1 (2) | XL1 (10) | PGMEA(30) | CyH(70) | 230° C./50 sec. | 130 | 0.44 |
| UDL-28 | Polymer 1 (7.5) | Additive 2 (7.5) | TAG1 (2) | XL1 (10) | PGMEA(30) | CyH(70) | 230° C./60 sec. | 130 | 0.44 |

TABLE 2-continued

| Formulation | Base polymer (pbw) | Additive (pbw) | Acid generator (pbw) | Crosslinker (pbw) | Solvent (pbw) | | Bake temp./ time | Refractive index at 193 nm | |
|---|---|---|---|---|---|---|---|---|---|
| | | | | | | | | n value | k value |
| UDL-29 | Polymer 2 (7.5) | Additive 2 (7.5) | TAG1 (2) | XL1 (10) | PGMEA(30) | CyH(70) | 230° C./60 sec. | 130 | 0.44 |
| UDL-30 | Polymer 3 (7.5) | Additive 2 (7.5) | TAG1 (2) | XL1 (10) | PGMEA(30) | CyH(70) | 230° C./60 sec. | 130 | 0.44 |
| Comparative UDL-31 | Comparative Polymer 9 (7.5) | — | — | — | PGMEA (100) | | 350° C./60 sec. | 1.31 | 0.44 |
| Comparative UDL-32 | Comparative Polymer 9 (7.5) | Additive 1 (7.5) | — | — | PGMEA (100) | | 350° C./60 sec. | 1.31 | 0.44 |
| Comparative UDL-33 | Comparative Polymer 9 (7.5) | Additive 2 (7.5) | — | — | PGMEA (100) | | 350° C./60 sec. | 1.31 | 0.44 |
| Comparative UDL-34 | Comparative Polymer 9 (7.5) | Additive 1 (7.5) | TAG1 (2) | XL1 (10) | PGMEA (100) | | 230° C./60 sec. | 1.31 | 0.44 |
| Comparative UDL-35 | Comparative Polymer 10 (7.5) | Comparative Polymer 9 (7.5) | TAG1 (2) | XL1 (10) | PGMEA (100) | | 230° C./60 sec. | 1.50 | 0.30 |
| Comparative UDL-36 | Comparative Polymer 10 (7.5) | Comparative Polymer 11 (7.5) | TAG1 (2) | XL1 (10) | PGMEA (100) | | 230° C./60 sec. | 1.50 | 0.30 |

PGMEA: propylene glycol monomethyl ether acetate
CyH: cyclohexanone

Measurement of Refractive Index

Each of the resist bottom layer material solutions formulated in Table 2 was coated onto a silicon substrate and baked at 350° C. for 60 seconds in the case of UDL-1 to 19 and Comparative UDL-31 to 33 or at 230° C. for 60 seconds in the case of UDL-20 to 30 and Comparative UDL-34 to 36, to form a bottom (or undercoat) layer of 200 nm thick. Using a variable angle spectroscopic ellipsometer (VASE®) of J. A. Woollam Co., the refractive index (n, k) at wavelength 193 nm of the bottom layers (UDL-1 to 30, Comparative UDL-31 to 36) was determined. The results are also shown in Table 2.

Examples 1 to 32 & Comparative Examples 1 to 6

Evaluation of Solvent Resistance

Loss of Film Thickness by Solvent Treatment

Each of the resist bottom layer material solutions (UDL-1 to 30 and Comparative UDL-31 to 36) was coated onto a silicon substrate and baked in air at the temperature shown in Table 3 for 60 seconds to form a bottom layer film. The film thickness was measured. PGMEA was dispensed on the film and kept thereon for 30 seconds, after which the substrate was spin dried and baked at 100° C. for 60 seconds for evaporating off the PGMEA. At this point, the film thickness was measured again, determining a difference in film thickness before and after PGMEA treatment. The results are shown in Table 3.

$CF_4/CHF_3$ Base Gas Etching Test

Each of the resist bottom layer material solutions (UDL-1 to 30 and Comparative UDL-31 to 36) was coated onto a silicon substrate and baked in air at the temperature shown in Table 3 for 60 seconds to form a bottom layer film of 350 nm thick. These bottom layer films were examined by a test of etching with $CF_4/CHF_3$ base gas using a dry etching instrument TE-8500P by Tokyo Electron, Ltd. A difference in thickness of the polymer film before and after the etching test was determined. The results are also shown in Table 3.

$CF_4/CHF_3$ Base Gas Etching Test

| | | |
|---|---|---|
| Chamber pressure | 40.0 | Pa |
| RF power | 1,000 | W |
| $CHF_3$ gas flow rate | 10 | ml/min |
| $CF_4$ gas flow rate | 100 | ml/min |
| He gas flow rate | 200 | ml/min |
| Time | 20 | sec |

In Table 3, a film thickness loss is reported in a relative value (percent), provided that the film thickness loss by $CF_4/CHF_3$ base gas etching in Comparative Example 1 is 100. A lower percent film thickness loss indicates greater etch resistance.

$O_2$ Base Gas Etching Test

Each of the resist bottom layer material solutions (UDL-1 to 30 and Comparative UDL-31 to 36) was coated onto a silicon substrate and baked in air at the temperature shown in Table 3 for 60 seconds to form a bottom layer film of 350 nm thick. These bottom layer films were examined by a test of etching with $O_2$ base gas using a dry etching instrument TE-8500P by Tokyo Electron, Ltd. A difference in thickness of the polymer film before and after the etching test was determined. The results are also shown in Table 3.

$O_2$ Base Gas Etching Test

| | | |
|---|---|---|
| Chamber pressure | 40.0 | Pa |
| RF power | 100 | W |
| $O_2$ gas flow rate | 30 | ml/min |
| $N_2$ gas flow rate | 70 | ml/min |
| Time | 60 | sec |

In Table 3, a film thickness loss is reported in a relative value (percent), provided that the film thickness loss by $O_2$ base gas etching in Comparative Example 1 is 100. A lower percent film thickness loss indicates greater etch resistance.

TABLE 3

| | | Formulation | Bake temp./time | Loss of film thickness by solvent treatment, Å | Loss of film thickness by CF$_4$/CHF$_3$ gas etching | | Loss of film thickness by O$_2$ gas etching | |
|---|---|---|---|---|---|---|---|---|
| | | | | | Å | percent loss based on film thickness loss in Comparative Example 1 = 100 | Å | percent loss based on film thickness loss in Comparative Example 1 = 100 |
| Example | 1 | UDL-1 | 350° C./60 sec. | 8 | 507 | 85% | 1972 | 90% |
| | 2 | UDL-1 | 400° C./60 sec. | 2 | 530 | 89% | 1959 | 90% |
| | 3 | UDL-2 | 400° C./60 sec. | 2 | 530 | 89% | 1958 | 90% |
| | 4 | UDL-3 | 350° C./60 sec. | 8 | 535 | 90% | 1980 | 91% |
| | 5 | UDL-4 | 400° C./60 sec. | 1 | 536 | 90% | 534 | 24% |
| | 6 | UDL-5 | 400° C./60 sec. | 2 | 525 | 88% | 1968 | 90% |
| | 7 | UDL-6 | 350° C./60 sec. | 12 | 509 | 86% | 1959 | 90% |
| | 8 | UDL-7 | 350° C./60 sec. | 3 | 539 | 91% | 1978 | 91% |
| | 9 | UDL-8 | 350° C./60 sec. | 3 | 538 | 90% | 1981 | 91% |
| | 10 | UDL-9 | 350° C./60 sec. | 11 | 529 | 89% | 1960 | 90% |
| | 11 | UDL-9 | 400° C./60 sec. | 10 | 525 | 88% | 1958 | 90% |
| | 12 | UDL-10 | 350° C./60 sec. | 3 | 518 | 87% | 1968 | 90% |
| | 13 | UDL-11 | 350° C./60 sec. | 5 | 534 | 90% | 1970 | 90% |
| | 14 | UDL-12 | 350° C./60 sec. | 7 | 539 | 91% | 1968 | 90% |
| | 15 | UDL-13 | 350° C./60 sec. | 1 | 541 | 91% | 1967 | 90% |
| | 16 | UDL-14 | 350° C./60 sec. | 1 | 515 | 87% | 1957 | 90% |
| | 17 | UDL-15 | 350° C./60 sec. | 2 | 544 | 91% | 1991 | 91% |
| | 18 | UDL-16 | 350° C./60 sec. | 1 | 534 | 90% | 1987 | 91% |
| | 19 | UDL-17 | 350° C./60 sec. | 10 | 521 | 88% | 1961 | 90% |
| | 20 | UDL-18 | 350° C./60 sec. | 9 | 524 | 88% | 1958 | 90% |
| | 21 | UDL-19 | 350° C./60 sec. | 7 | 530 | 89% | 1960 | 90% |
| | 22 | UDL-20 | 230° C./60 sec. | 2 | 551 | 93% | 1982 | 91% |
| | 23 | UDL-21 | 230° C./60 sec. | 1 | 552 | 93% | 1980 | 91% |
| | 24 | UDL-22 | 230° C./60 sec. | 3 | 550 | 92% | 1982 | 91% |
| | 25 | UDL-23 | 230° C./60 sec. | 1 | 558 | 94% | 1991 | 91% |
| | 26 | UDL-24 | 230° C./60 sec. | 2 | 556 | 93% | 1990 | 91% |
| | 27 | UDL-25 | 230° C./60 sec. | 3 | 557 | 94% | 1981 | 91% |
| | 28 | UDL-26 | 230° C./60 sec. | 2 | 557 | 94% | 1992 | 91% |
| | 29 | UDL-27 | 230° C./60 sec. | 4 | 556 | 93% | 1990 | 91% |
| | 30 | UDL-28 | 230° C./60 sec. | 2 | 548 | 92% | 1980 | 91% |
| | 31 | UDL-29 | 230° C./60 sec. | 3 | 549 | 92% | 1983 | 91% |
| | 32 | UDL-30 | 230° C./60 sec. | 1 | 550 | 92% | 1984 | 91% |
| Comparative Example | 1 | Comparative UDL-31 | 350° C./60 sec. | 2 | 595 | 100% | 2180 | 100% |
| | 2 | Comparative UDL-32 | 350° C./60 sec. | 3 | 570 | 96% | 2040 | 94% |
| | 3 | Comparative UDL-33 | 350° C./60 sec. | 5 | 575 | 97% | 2050 | 94% |
| | 4 | Comparative UDL-34 | 230° C./60 sec. | 5 | 590 | 99% | 2123 | 97% |
| | 5 | Comparative UDL-35 | 230° C./60 sec. | 2 | 574 | 96% | 2151 | 99% |
| | 6 | Comparative UDL-36 | 230° C./60 sec. | 1 | 560 | 94% | 2201 | 101% |

Preparation of Silicon-Containing Middle Layer-Coating Solution

A silicon-containing middle layer-coating solution was prepared by dissolving 2.0 parts by weight of a silicon-containing polymer, shown below, in 100 parts by weight of a solvent PGMEA containing 0.1 wt % of surfactant FC-4430 (3M-Sumitomo Co., Ltd.) and filtering through a fluoroplastic filter having a pore size of 0.1 μm. The solution was coated onto the bottom layer. A middle layer film resulting from the silicon-containing middle layer-coating solution is designated SiL-1.

Silicon-Containing Polymer:

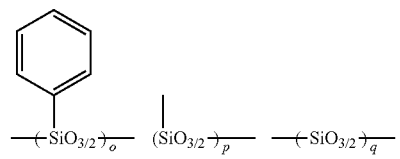

Silicon-containing middle layer polymer
(o = 0.20, p = 0.50. q = 0.30, Mw = 3,400)

Preparation of Resist Top Layer Material and Protective Film for Immersion Lithography A resist top layer material was prepared by dissolving a resin, acid generator and basic compound in a solvent containing 0.1 wt % of surfactant FC-4430 (3M-Sumitomo Co., Ltd.) in accordance with the formulation shown in Table 4 and filtering through a fluoroplastic filter having a pore size of 0.1 μm. In Tables 4 and 6, this resist top layer material is designated SL resist for ArF.

TABLE 4

|  | Resin (pbw) | Acid generator (pbw) | Basic compound (pbw) | Solvent (pbw) |
|---|---|---|---|---|
| SL resist for ArF | ArF single-layer resist polymer (100) | PAG1 (6.6) | TMMEA (0.8) | PGMEA (2,500) |

The ArF single-layer resist polymer, PAG1, and TMMEA in Table 4 are identified below.

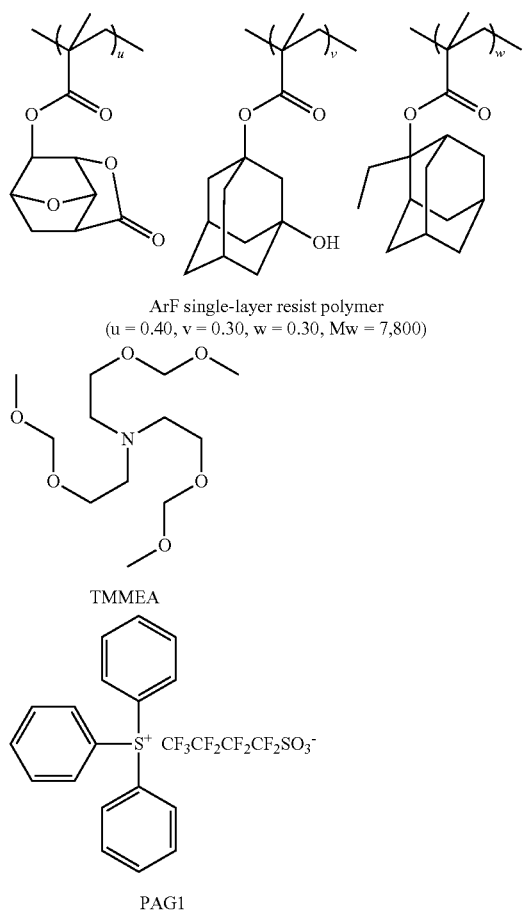

A protective film (TC-1) for immersion lithography was prepared by dissolving a resin in a solvent in accordance with the formulation shown in Table 5 and filtering through a fluoroplastic filter having a pore size of 0.1 μm.

TABLE 5

|  | Resin (pbw) | Organic solvent (pbw) |
|---|---|---|
| TC-1 | protective film polymer (100) | diisoamyl ether (2,700) 2-methyl-1-butanol (270) |

The protective film polymer in Table 5 is identified below.

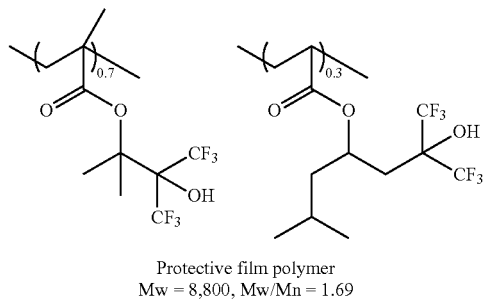

Protective film polymer
Mw = 8,800, Mw/Mn = 1.69

Pattern Etching Test

Examples 33 to 62 & Comparative Examples 7 to 12

The bottom layer material (UDL-1 to 30, Comparative UDL-31 to 36) was coated onto a silicon wafer (diameter 300 mm) having a SiO₂ film of 200 nm thick deposited thereon, and baked under the conditions shown in Table 6 to form a resist bottom layer of 200 nm thick. The bake of the resist bottom layer was done in an air atmosphere.

Formation of Silicon-Containing Resist Middle Layer SiL-1

The silicon-containing resist middle layer material SiL-1 was coated onto the resist bottom layer and baked at 200° C. for 60 seconds to form a resist middle layer of 35 nm thick.

Formation of Resist Top Layer (SL Resist for ArF) and Protective Film

The resist top layer material (SL resist for ArF in solution form) shown in Table 4 was coated on the bottom layer and baked at 105° C. for 60 seconds to form a resist top layer of 100 nm thick. The protective film (TC-1) for immersion lithography was coated on the resist top layer and baked at 90° C. for 60 seconds to form a protective film of 50 nm thick.

Patterning by Immersion Lithography

The resist top layer was exposed using an ArF immersion lithography exposure tool NSR-S610C (Nikon Corporation, NA 1.30, σ0.98/0.65, 35° dipole polarized illumination, 6% halftone phase shift mask), baked (PEB) at 100° C. for 60 seconds, and developed for 30 seconds with a 2.38 wt % aqueous solution of tetramethylammonium hydroxide (TMAH), thereby forming a positive 43 nm 1:1 line-and-space pattern.

Etching Test After Patterning

The structure was dry etched using an etching instrument Telius by Tokyo Electron, Ltd. First, the silicon-containing resist middle layer (SOG) was processed through the resist pattern as mask. Then the resist bottom layer was processed through the resulting silicon-containing resist middle layer pattern as mask. Finally, the SiO₂ film was processed through the resulting resist bottom layer pattern as mask. The etching conditions are shown below.

Transfer of Resist Pattern to Silicon-Containing Resist Middle Layer

| | |
|---|---|
| Chamber pressure | 10.0 Pa |
| RF power | 1,500 W |
| CF$_4$ gas flow rate | 75 ml/min |
| O$_2$ gas flow rate | 15 ml/min |
| Time | 15 sec |

Transfer of Silicon-Containing Middle Layer Pattern to Bottom Layer

| | |
|---|---|
| Chamber pressure | 2.0 Pa |
| RF power | 500 W |
| Ar gas flow rate | 75 ml/min |
| O$_2$ gas flow rate | 45 ml/min |
| Time | 120 sec |

Transfer of Bottom Layer Pattern to SiO$_2$ Film

| | |
|---|---|
| Chamber pressure | 2.0 Pa |
| RF power | 2,200 W |
| C$_5$F$_{12}$ gas flow rate | 20 ml/min |
| C$_2$F$_6$ gas flow rate | 10 ml/min |
| Ar gas flow rate | 300 ml/min |
| O$_2$ gas flow rate | 60 ml/min |
| Time | 90 sec |

The cross-sectional profile of the patterns was observed under electron microscope S-4700 (Hitachi, Ltd.). The results are shown in Table 6.

TABLE 6

| | | Bottom layer formulation | Bottom layer bake temp./time | Resist/middle layer | Pattern profile after development | Pattern profile after etching transfer to middle layer | Pattern profile after etching transfer to bottom layer | Pattern profile after etching transfer to substrate | Pattern twist after etching transfer to substrate |
|---|---|---|---|---|---|---|---|---|---|
| Example | 33 | UDL-1 | 350° C./60 sec. | SL resist for ArF/SiL-1 | perpendicular | perpendicular | perpendicular | perpendicular | nil |
| | 34 | UDL-2 | 350° C./60 sec. | SL resist for ArF/SiL-1 | perpendicular | perpendicular | perpendicular | perpendicular | nil |
| | 35 | UDL-3 | 350° C./60 sec. | SL resist for ArF/SiL-1 | perpendicular | perpendicular | perpendicular | perpendicular | nil |
| | 36 | UDL-4 | 350° C./60 sec. | SL resist for ArF/SiL-1 | perpendicular | perpendicular | perpendicular | perpendicular | nil |
| | 37 | UDL-5 | 350° C./60 sec. | SL resist for ArF/SiL-1 | perpendicular | perpendicular | perpendicular | perpendicular | nil |
| | 38 | UDL-6 | 350° C./60 sec. | SL resist for ArF/SiL-1 | perpendicular | perpendicular | perpendicular | perpendicular | nil |
| | 39 | UDL-7 | 350° C./60 sec. | SL resist for ArF/SiL-1 | perpendicular | perpendicular | perpendicular | perpendicular | nil |
| | 40 | UDL-8 | 350° C./60 sec. | SL resist for ArF/SiL-1 | perpendicular | perpendicular | perpendicular | perpendicular | nil |
| | 41 | UDL-9 | 350° C./60 sec. | SL resist for ArF/SiL-1 | perpendicular | perpendicular | perpendicular | perpendicular | nil |
| | 42 | UDL-10 | 350° C./60 sec. | SL resist for ArF/SiL-1 | perpendicular | perpendicular | perpendicular | perpendicular | nil |
| | 43 | UDL-11 | 350° C./60 sec. | SL resist for ArF/SiL-1 | perpendicular | perpendicular | perpendicular | perpendicular | nil |
| | 44 | UDL-12 | 350° C./60 sec. | SL resist for ArF/SiL-1 | perpendicular | perpendicular | perpendicular | perpendicular | nil |
| | 45 | UDL-13 | 350° C./60 sec. | SL resist for ArF/SiL-1 | perpendicular | perpendicular | perpendicular | perpendicular | nil |
| | 46 | UDL-14 | 350° C./60 sec. | SL resist for ArF/SiL-1 | perpendicular | perpendicular | perpendicular | perpendicular | nil |
| | 47 | UDL-15 | 350° C./60 sec. | SL resist for ArF/SiL-1 | perpendicular | perpendicular | perpendicular | perpendicular | nil |
| | 48 | UDL-16 | 230° C./60 sec. | SL resist for ArF/SiL-1 | perpendicular | perpendicular | perpendicular | perpendicular | nil |
| | 49 | UDL-17 | 230° C./60 sec. | SL resist for ArF/SiL-1 | perpendicular | perpendicular | perpendicular | perpendicular | nil |
| | 50 | UDL-18 | 230° C./60 sec. | SL resist for ArF/SiL-1 | perpendicular | perpendicular | perpendicular | perpendicular | nil |
| | 51 | UDL-19 | 230° C./60 sec. | SL resist for ArF/SiL-1 | perpendicular | perpendicular | perpendicular | perpendicular | nil |
| | 52 | UDL-20 | 230° C./60 sec. | SL resist for ArF/SiL-1 | perpendicular | perpendicular | perpendicular | perpendicular | nil |
| | 53 | UDL-21 | 230° C./60 sec. | SL resist for ArF/SiL-1 | perpendicular | perpendicular | perpendicular | perpendicular | nil |
| | 54 | UDL-22 | 230° C./60 sec. | SL resist for ArF/SiL-1 | perpendicular | perpendicular | perpendicular | perpendicular | nil |
| | 55 | UDL-23 | 230° C./60 sec. | SL resist for ArF/SiL-1 | perpendicular | perpendicular | perpendicular | perpendicular | nil |
| | 56 | UDL-24 | 230° C./60 sec. | SL resist for ArF/SiL-1 | perpendicular | perpendicular | perpendicular | perpendicular | nil |
| | 57 | UDL-25 | 230° C./60 sec. | SL resist for ArF/SiL-1 | perpendicular | perpendicular | perpendicular | perpendicular | nil |

TABLE 6-continued

| | | Bottom layer formulation | Bottom layer bake temp./time | Resist/middle layer | Pattern profile after development | Pattern profile after etching transfer to middle layer | Pattern profile after etching transfer to bottom layer | Pattern profile after etching transfer to substrate | Pattern twist after etching transfer to substrate |
|---|---|---|---|---|---|---|---|---|---|
| | 58 | UDL-26 | 230° C./60 sec. | SL resist for ArF/SiL-1 | perpendicular | perpendicular | perpendicular | perpendicular | nil |
| | 59 | UDL-27 | 230° C./60 sec. | SL resist for ArF/SiL-1 | perpendicular | perpendicular | perpendicular | perpendicular | nil |
| | 60 | UDL-28 | 230° C./60 sec. | SL resist for ArF/SiL-1 | perpendicular | perpendicular | perpendicular | perpendicular | nil |
| | 61 | UDL-29 | 230° C./60 sec. | SL resist for ArF/SiL-1 | perpendicular | perpendicular | perpendicular | perpendicular | nil |
| | 62 | UDL-30 | 230° C./60 sec. | SL resist for ArF/SiL-1 | perpendicular | perpendicular | perpendicular | perpendicular | nil |
| Comparative Example | 7 | Comparative UDL-31 | 350° C./60 sec. | SL resist for ArF/SiL-1 | perpendicular | perpendicular | perpendicular | perpendicular | heavy twists observed |
| | 8 | Comparative UDL-32 | 350° C./60 sec. | SL resist for ArF/SiL-1 | perpendicular | perpendicular | perpendicular | perpendicular | heavy twists observed |
| | 9 | Comparative UDL-33 | 350° C./60 sec. | SL resist for ArF/SiL-1 | perpendicular | perpendicular | perpendicular | perpendicular | heavy twists observed |
| | 10 | Comparative UDL-34 | 230° C./60 sec. | SL resist for ArF/SiL-1 | perpendicular | perpendicular | perpendicular | perpendicular | heavy twists observed |
| | 11 | Comparative UDL-35 | 230° C./60 sec. | SL resist for ArF/SiL-1 | perpendicular | perpendicular | perpendicular | perpendicular | heavy twists observed |
| | 12 | Comparative UDL-36 | 230° C./60 sec. | SL resist for ArF/SiL-1 | perpendicular | perpendicular | perpendicular | tapered | heavy twists observed |

Burying of Stepped Substrate

Examples 63, 64 & Comparative Examples 13, 14

On a $SiO_2$ deposited stepped substrate in the form of a silicon substrate having a densely packed hole pattern having a thickness of 500 nm and a diameter of 160 nm formed thereon, a bottom layer material (UDL-9, 17, Comparative UDL-31, 32) was coated and baked at 350° C. for 60 seconds so as to form a bottom layer of 200 nm thick as measured from the flat substrate. The coated substrate was sectioned and observed under SEM whether or not the holes were filled with the film material down to the bottom. The results are shown in Table 7.

TABLE 7

| | | Bottom layer formulation | Bottom layer bake temp./time | Burying property |
|---|---|---|---|---|
| Example | 63 | UDL-9 | 350° C./60 sec. | holes fully filled to bottom |
| | 64 | UDL-17 | 350° C./60 sec. | holes fully filled to bottom |
| Comparative Example | 13 | Comparative UDL-31 | 350° C./60 sec. | some bury failures |
| | 14 | Comparative UDL-32 | 350° C./60 sec. | holes fully filled to bottom |

Outgas Test

Examples 65 to 67 & Comparative Examples 15, 16

A bottom layer material (UDL-1, 9, 17, Comparative UDL-31, 32) was coated on a silicon substrate and baked at 350° C. for 60 seconds to form a bottom layer of 200 nm thick. When particulate emissions were observed in a hot plate oven during the 350° C. bake, the number of particles with a size of 0.3 μm and 0.5 μm was counted using a particle counter KR-11A (Rion Co., Ltd.). The results are shown in Table 8.

TABLE 8

| | | Bottom layer formulation | Bottom layer bake temp./time | 0.3 μm particles | 0.5 μm particles |
|---|---|---|---|---|---|
| Example | 65 | UDL-1 | 350° C./60 sec. | 0 | 0 |
| | 66 | UDL-9 | 350° C./60 sec. | 10 | 2 |
| | 67 | UDL-17 | 350° C./60 sec. | 3 | 1 |
| Comparative Example | 15 | Comparative UDL-31 | 350° C./60 sec. | 501 | 120 |
| | 16 | Comparative UDL-32 | 350° C./60 sec. | 1,010 | 621 |

It is seen from Table 2 that the resist bottom layer film formed by the inventive method has such a refractive index that the film may be practically used as the resist bottom layer film in the trilayer process for immersion lithography.

It is seen from Table 3 that baking at a temperature in excess of 350° C. results in a resist bottom layer which is insoluble in the solvent (Examples 1 to 21).

It is seen from Table 3 that when thermal acid generator TAG1 and crosslinker XL1 shown in Table 1-3 are used, a resist bottom layer which is insoluble in the solvent can be formed even by low-temperature baking (Examples 22 to 32).

As is evident from Table 6, the rates of $CF_4/CHF_3$ gas etching and $O_2$ gas etching of the resist bottom layer formed by the inventive method are lower than Comparative Polymers 9 to 11 (Comparative UDL-31 to 36), indicating very high etch resistance.

It is seen from Table 6 that when the resist bottom layer formed by the inventive method was used, the resist profile after development and the profile of the bottom layer after oxygen etching and after substrate etching were improved, and the patterns were observed to be free of twists (Examples 33 to 62).

As seen from Table 7, a burying failure is found in Comparative Example 13. In contrast, burying property is improved by adding monomeric Additive 1 or Additive 2 to the resist bottom layer material. However, the addition of the monomer gives rise to a problem that particles are emitted during bake to contaminate the hot plate oven as seen from Comparative Examples 15, 16 in Table 8. The resist bottom layer formed from the resist bottom layer material comprising the naphthalene derivative as defined herein has both the advantages of step burying and particle prevention because particulate emission is avoided even when a monomer or low molecular weight compound is added in a relatively large amount.

While the invention has been illustrated and described in typical embodiments, it is not intended to be limited to the details shown. Various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims.

Japanese Patent Application No. 2010-140533 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A naphthalene derivative having the general formula (1):

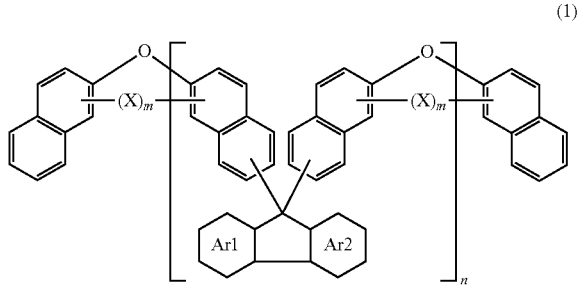

wherein cyclic structures Ar1 and Ar2 denote a benzene or naphthalene ring, X is a single bond or $C_1$-$C_{20}$ alkylene, m is 0 or 1, and n is such a natural number as to provide a molecular weight of up to 100,000.

2. A naphthalene derivative comprising a partial structure having the general formula (2):

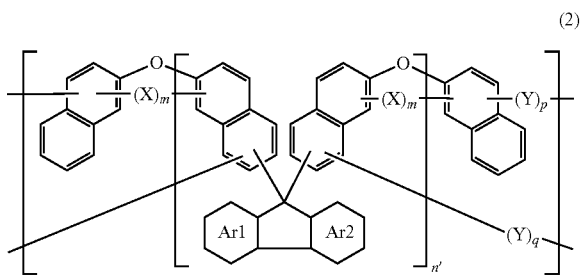

wherein cyclic structures Ar1 and Ar2 denote a benzene or naphthalene ring, X is a single bond or $C_1$-$C_{20}$ alkylene, m is 0 or 1, Y is a single bond or $C_1$-$C_{20}$ alkylene, p and q each are 0 or a natural number, with the proviso that p and q are not equal to 0 at the same time, and n' is such a natural number as to provide a molecular weight of up to 200,000.

3. A resist bottom layer material comprising a naphthalene derivative having the general formula (1):

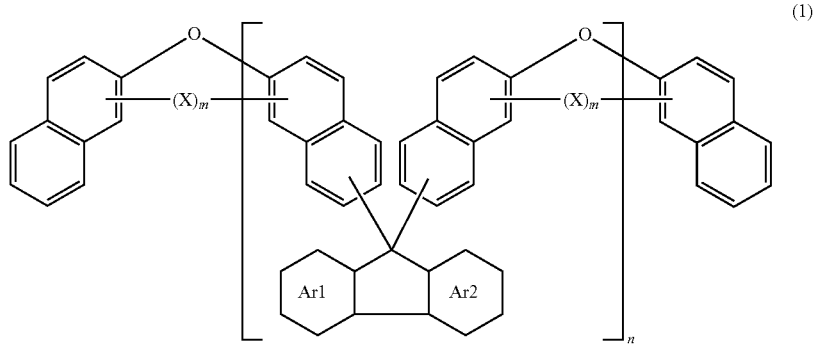

wherein cyclic structures Ar1 and Ar2 denote a benzene or naphthalene ring, X is a single bond or $C_1$-$C_{20}$ alkylene, m is 0 or 1, and n is such a natural number as to provide a molecular weight of up to 100,000, or a naphthalene derivative comprising a partial structure having the general formula (2):

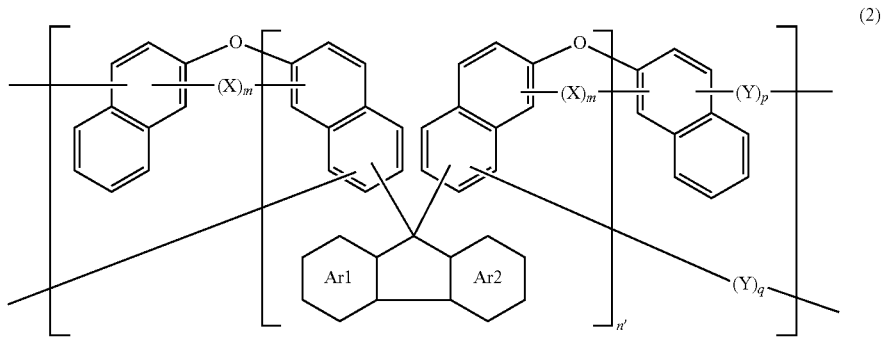

(2)

wherein cyclic structures Ar1 and Ar2 denote a benzene or naphthalene ring, X is a single bond or $C_1$-$C_{20}$ alkylene, m is 0 or 1, Y is a single bond or $C_1$-$C_{20}$ alkylene, p and q each are 0 or a natural number, with the proviso that p and q are not equal to 0 at the same time, and n' is such a natural number as to provide a molecular weight of up to 200,000, or a polymer comprising the naphthalene derivative.

4. A method for forming a resist bottom layer which is included in a multilayer resist film of at least three layers used in the lithography, comprising the steps of:
coating a resist bottom layer material onto a substrate, and
heat treating the coating of resist bottom layer material at a temperature of more than 150° C. to 600° C. for 10 to 600 seconds for curing,
wherein the resist bottom layer material comprises a naphthalene derivative having the general formula (1):

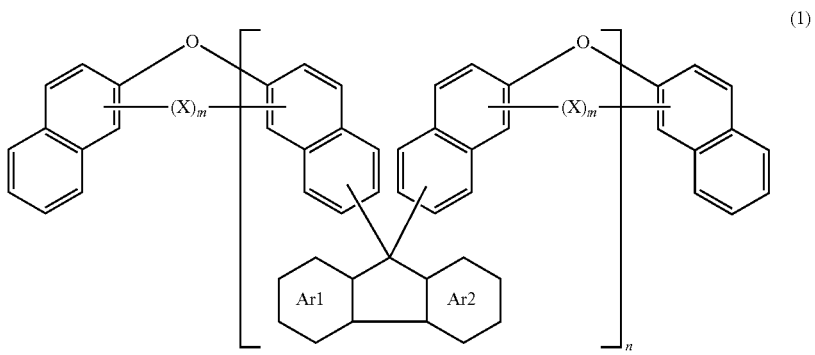

(1)

wherein cyclic structures Ar1 and Ar2 denote a benzene or naphthalene ring, X is a single bond or $C_1$-$C_{20}$ alkylene, m is 0 or 1, and n is such a natural number as to provide a molecular weight of up to 100,000, or a naphthalene derivative comprising a partial structure having the general formula (2):

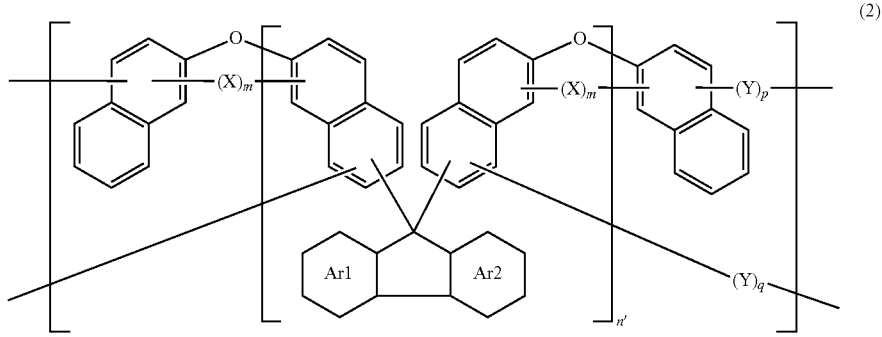

(2)

wherein cyclic structures Ar1 and Ar2 denote a benzene or naphthalene ring, X is a single bond or $C_1$-$C_{20}$ alkylene, m is 0 or 1, Y is a single bond or $C_1$-$C_{20}$ alkylene, p and q each are 0 or a natural number, with the proviso that p and q are not equal to 0 at the same time, and n' is such a natural number as to provide a molecular weight of up to 200,000, or a polymer comprising one or both of the naphthalene derivatives.

5. The method of claim 4 wherein the step of coating the resist bottom layer material onto a substrate is performed by spin coating.

6. The method of claim 4 wherein the resist bottom layer material further comprises an organic solvent.

7. The method of claim 4 wherein the resist bottom layer material further comprises a crosslinker and an acid generator.

8. A process for forming a pattern in a substrate by lithography, comprising at least the steps of:
forming a resist bottom layer on a substrate by the method of claim 4,
forming a resist middle layer on the resist bottom layer using a silicon-containing resist middle layer material,
forming a resist top layer on the resist middle layer using a resist top layer material which is a photoresist composition,
exposing a pattern circuit region of the resist top layer to radiation,
developing the resist top layer with a developer to form a resist pattern therein,
etching the resist middle layer using the resist pattern as an etching mask,
etching the resist bottom layer using the resulting resist middle layer pattern as an etching mask, and
etching the substrate using the resulting resist bottom layer pattern as an etching mask.

9. A process for forming a pattern in a substrate by lithography, comprising at least the steps of:
forming a resist bottom layer on a substrate by the method of claim 4,
forming on the resist bottom layer an inorganic hard mask middle layer which is selected from a silicon oxide film, silicon nitride film, and silicon oxynitride film,
forming a resist top layer on the inorganic hard mask middle layer using a resist top layer material which is a photoresist composition,
exposing a pattern circuit region of the resist top layer to radiation,
developing the resist top layer with a developer to form a resist pattern therein,
etching the inorganic hard mask middle layer using the resist pattern as an etching mask,
etching the resist bottom layer using the resulting inorganic hard mask middle layer pattern as an etching mask, and
etching the substrate using the resulting resist bottom layer pattern as an etching mask.

10. A process for forming a pattern in a substrate by lithography, comprising at least the steps of:
forming a resist bottom layer on a substrate by the method of claim 4,
forming on the resist bottom layer an inorganic hard mask middle layer which is selected from a silicon oxide film, silicon nitride film, and silicon oxynitride film,
forming an organic ARC film on the inorganic hard mask middle layer,
forming a resist top layer on the organic ARC film using a resist top layer material which is a photoresist composition,
exposing a pattern circuit region of the resist top layer to radiation,
developing the resist top layer with a developer to form a resist pattern therein,
etching the organic ARC film and inorganic hard mask middle layer using the resist pattern as an etching mask,
etching the resist bottom layer using the resulting inorganic hard mask middle layer pattern as an etching mask, and
etching the substrate using the resulting resist bottom layer pattern as an etching mask.

11. The pattern forming process of claim 9 wherein the step of forming an inorganic hard mask middle layer is performed by CVD or ALD.

12. The pattern forming process of claim 8 wherein the resist top layer material is free of a silicon-containing polymer, and the step of etching the resist bottom layer using the middle layer pattern as an etching mask uses an oxygen or hydrogen-based etchant gas.

13. The naphthalene derivative of claim 1, wherein m is 1.

14. The naphthalene derivative of claim 2, wherein m is 1.

* * * * *